(12) United States Patent
Kol et al.

(10) Patent No.: US 9,200,099 B2
(45) Date of Patent: Dec. 1, 2015

(54) SALENOL CATALYST

(71) Applicants:ExxonMobil Chemical Patents Inc., Baytown, TX (US); Ramot at Tel-Aviv University Ltd., Tel Aviv (IL)

(72) Inventors: Moshe Kol, Ramat Gan (IL); Konstantin Press, Rishon LeZion (IL); Matthew W. Holtcamp, Huffman, TX (US)

(73) Assignees: ExxonMobil Chemical Patents Inc., Baytown, TX (US); Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 14/289,186

(22) Filed: May 28, 2014

(65) Prior Publication Data

US 2014/0378635 A1    Dec. 25, 2014

Related U.S. Application Data

(60) Provisional application No. 61/837,588, filed on Jun. 20, 2013.

(51) Int. Cl.
| | | |
|---|---|---|
| C08F 110/06 | (2006.01) | |
| C08F 4/64 | (2006.01) | |
| C07F 7/00 | (2006.01) | |
| C08F 4/60 | (2006.01) | |

(52) U.S. Cl.
CPC ............... *C08F 110/06* (2013.01); *C07F 7/006* (2013.01); *C08F 4/64189* (2013.01); *C08F 4/60189* (2013.01)

(58) Field of Classification Search
CPC . C08F 4/60189; C08F 110/06; C08F 4/64189

USPC .................................................. 526/172, 351
See application file for complete search history.

(56) References Cited

U.S. PATENT DOCUMENTS

| | | | |
|---|---|---|---|
| 4,066,715 | A | 1/1978 | Isa et al. |
| 5,153,157 | A | 10/1992 | Hlatky et al. |
| 5,942,459 | A | 8/1999 | Sugano et al. |
| 6,309,997 | B1 | 10/2001 | Fujita et al. |
| 6,399,724 | B1 | 6/2002 | Matsui et al. |
| 6,462,136 | B1 | 10/2002 | Saito |
| 6,531,555 | B2 | 3/2003 | Whiteker |

(Continued)

FOREIGN PATENT DOCUMENTS

| | | |
|---|---|---|
| CN | 101080399 | 11/2007 |
| CN | 101437827 | 5/2009 |

(Continued)

OTHER PUBLICATIONS

Plass, W. Zeitschrifte fur Anorganische und Allgemeine Chemie 1997, 623(6), 997-1005.*

(Continued)

*Primary Examiner* — Rip A Lee
(74) *Attorney, Agent, or Firm* — Daniel N. Lundeen; Lundeen & Lundeen PLLC

(57) ABSTRACT

Catalysts comprising salenol ligands are disclosed herein. Also, catalyst systems comprising the catalyst and an activator; methods to prepare the ligands, catalysts and catalyst systems; processes to polymerize olefins using the catalysts and/or catalyst systems; and the olefin polymers prepared according to the processes.

25 Claims, 1 Drawing Sheet

(56) References Cited

U.S. PATENT DOCUMENTS

| | | | |
|---|---|---|---|
| 6,548,723 B2 | 4/2003 | Bagheri et al. | |
| 6,632,899 B2 | 10/2003 | Kol et al. | |
| 6,686,490 B1 | 2/2004 | Kol et al. | |
| 6,699,824 B1 | 3/2004 | Dawson et al. | |
| 7,105,703 B1 | 9/2006 | Atwood | |
| 7,144,839 B2 | 12/2006 | Gibson et al. | |
| 7,241,714 B2 | 7/2007 | Boussie et al. | |
| 7,300,903 B2 | 11/2007 | Fujita et al. | |
| 7,385,015 B2 | 6/2008 | Holtcamp | |
| 7,531,602 B2 | 5/2009 | Hoang et al. | |
| 7,544,749 B2 | 6/2009 | Jones et al. | |
| 7,696,123 B2 | 4/2010 | Schneider et al. | |
| 7,812,184 B2 | 10/2010 | Kondo et al. | |
| 7,880,047 B2 | 2/2011 | Knowles et al. | |
| 7,989,565 B2 | 8/2011 | Gibson et al. | |
| 8,058,373 B2 | 11/2011 | Stevens et al. | |
| 8,101,696 B2 | 1/2012 | Konze et al. | |
| 8,202,953 B2 | 6/2012 | Konze et al. | |
| 8,222,358 B2 | 7/2012 | Rodriguez et al. | |
| 8,299,189 B2 | 10/2012 | Boone et al. | |
| 8,450,438 B2 | 5/2013 | Aboelella et al. | |
| 8,907,032 B2 * | 12/2014 | Kol et al. | 526/172 |
| 2002/0173604 A1 | 11/2002 | Kol et al. | |
| 2003/0105250 A1 | 6/2003 | Whiteker | |
| 2004/0167016 A1 | 8/2004 | Holtcamp et al. | |
| 2005/0075242 A1 | 4/2005 | Holtcamp et al. | |
| 2005/0227860 A1 | 10/2005 | Green et al. | |
| 2006/0100092 A1 | 5/2006 | Jones et al. | |
| 2007/0021561 A1 | 1/2007 | Tse et al. | |
| 2007/0208148 A1 | 9/2007 | Rodriguez et al. | |
| 2008/0108499 A1 | 5/2008 | Coates et al. | |
| 2009/0043100 A1 | 2/2009 | Kondo et al. | |
| 2009/0099381 A1 | 4/2009 | Katsuki et al. | |
| 2009/0186995 A1 | 7/2009 | Canich et al. | |
| 2009/0318640 A1 | 12/2009 | Brant et al. | |
| 2009/0318644 A1 | 12/2009 | Brandt et al. | |
| 2010/0029871 A1 | 2/2010 | Crowther et al. | |
| 2010/0081808 A1 | 4/2010 | Kondo et al. | |
| 2010/0298510 A1 | 11/2010 | Crowther et al. | |
| 2011/0124831 A1 | 5/2011 | Luo | |
| 2011/0152497 A1 | 6/2011 | Allen et al. | |
| 2011/0306740 A1 | 12/2011 | Nagy et al. | |
| 2011/0319578 A1 | 12/2011 | Hanaoka et al. | |
| 2012/0184676 A1 | 7/2012 | Gahleitner et al. | |
| 2012/0245312 A1 | 9/2012 | Holtcamp | |
| 2012/0316302 A1 | 12/2012 | Stewart | |
| 2013/0030135 A1 | 1/2013 | Hagadorn et al. | |
| 2013/0096271 A1 | 4/2013 | Kol et al. | |
| 2013/0253244 A1 | 9/2013 | Emett et al. | |
| 2013/0310529 A1 | 11/2013 | Kol et al. | |
| 2014/0039137 A1 | 2/2014 | Giesbrecht et al. | |
| 2014/0039138 A1 | 2/2014 | Giesbrecht et al. | |
| 2014/0039139 A1 | 2/2014 | Giesbrecht et al. | |
| 2014/0039140 A1 | 2/2014 | Giesbrecht et al. | |
| 2014/0039141 A1 | 2/2014 | Giesbrecht et al. | |

FOREIGN PATENT DOCUMENTS

| | | | |
|---|---|---|---|
| CN | 101080399 | 12/2012 | |
| EP | 1849778 | 10/2007 | |
| EP | 2003135 | 12/2008 | |
| EP | 2532687 | 12/2012 | |
| JP | 2007284438 | 11/2007 | |
| WO | 9806727 | 2/1998 | |
| WO | 0236638 | 5/2002 | |
| WO | 03091292 | 11/2003 | |
| WO | 2004069881 | 8/2004 | |
| WO | 2007007893 | 1/2007 | |
| WO | 2009027516 | 3/2009 | |
| WO | 2011019474 | 2/2011 | |
| WO | 2011058241 | 12/2011 | |
| WO | WO 2011/158241 A1 * | 12/2011 | C07F 7/00 |
| WO | 2012004680 | 1/2012 | |
| WO | 2012098521 | 1/2012 | |
| WO | 2012098521 | 9/2012 | |
| WO | 2013043796 | 3/2013 | |

OTHER PUBLICATIONS

Rajendiran et al. Inorg. Chem., 2007, 46(25), 10446-10448.*

PCT/US2013/046569 International Search Report and Written Opinion, Jun. 13, 2014.

PCT/US2013/046615 International Search Report and Written Opinion, Nov. 13, 2013.

PCT/US2013/053363 International Search Report and Written Opinion, Dec. 20, 2013.

PCT/US2013/69419 International Search Report and Written Opinion, Mar. 7, 2014.

Berkessel, Albrecht et al., Ligands: Highly Enantioselective Titanium In Situ Catalysts for Asymmetric Epoxidation with Aqueous Hydrogen Peroxide, Adv. Synth Catal, 2007, vol. 349, pp. 2385-2391.

Whitelaw, Emma L. et al., Group 4 Salalen Complexes and Their Application for the Ring-Opening Polymerization of rac-Lactide, Inorg. Chem., 2010, vol. 49, pp. 7176-7181.

Arredondo, Yolanda et al., Non-Catalyzed C-Alkylation of Phenols with Cyclic Secondary Alkyl Bromies, Synthetic Communications, 1996, vol. 26, No. 21, pp. 3885-3895.

Bryliakov, K. et al, Titanium-Salan-Catalyzed Asymmetric Oxidation of Sulfides and Kinetic Resolution of Sulfoxides with H2O2 as the Oxidant, Eur. J. Org. Chem., 2008, pp. 3369-3376.

Busico, Vincenzo et al, New Evidence on the Nature of the Active Sites in Heterogeneous Ziegler-Natta Catalysts for Propene Polymerization, 1997, Macromolecules, vol. 30, pp. 4786-4790.

Busico, Vincenzo et al., Mimicking Ziegler-Natta Catalysts in Homogeneous Phase, 1 C2-Symmetric Octahedral Zr (IV) Complexes with Tetradentate [ONNO]-Type Ligands, Macromol. Rapid Commun. 2001, vol. 22, No. 17, pp. 1405-1409.

Busico, Vincenzo et al., The first Molecularly Characterized Isotactic Polypropylene-block-polyethylene Obtained via "Quasi-Living" Insertion Polymerization, Macromolecules, 2003, vol. 36, No. 11, pp. 3806-3808.

Busico, Vincenzo et al., Block Copolymers of Highly Isotactic Polypropylene via Controlled Ziegler-Natta Polymerization, Macromolecules, 2004, vol. 37, No. 22, pp. 8201-8203.

Busico, Vincenzo et al., Design of stereoselective Ziegler-Natta propene polymerization catalysts, PNAS, 2006, vol. 103, No. 42, pp. 15321-15326.

Ciancaleoni, Gianluca et al., Structure/Properties Relationship for Bis{phenoxyamine)Zr(IV)-Based Olefin Polymerization Catalysts: A Simple OFT Model to Predict Catalytic Activity, Macromolecules, 2012, vol. 45, pp. 4046-4053.

Cipullo, Roberta et al., Improving the Behavior of Bis(phenoxyamine) Group 4 Metal Catalysts for Controlled Alkene Polymerization, 2009, Macromolecules, vol. 42, pp. 3869-3872.

Clarkson, Guy et al., Group 4 catalysts for ethene polymerization containing tetradentate salicylaldiminato ligands, 2006, Dalton Trans., pp. 5484-5491.

Cohen, AD et al., Construction of C1-symmetric zirconium complexes by the design of new Salan ligands. Coordination chemistry and preliminary polymerisation catalysis studies, Chem. Commun, 2008, pp. 2149-2151.

Cohen, AD et al., C1-Symmetric Zirconium Complexes of [ONNO#]-Type Salan Ligands: Accurate Control of Catalyst Activity, Isospecificity, and Molecular Weight in 1-Hexene Polymerization, Organometallics, 2009, vol. 28, No. 5, pp. 1391-1405.

Cohen, AD et al., Same Ligand, Different Metals: Diiodo-Salan Complexes of the Group 4 Triad in Isospecific Polymerization of 1-Hexene and Propylene, Macromolecules, 2010, vol. 43, No. 4, pp. 1689-1691.

Corradini, Paolo et al., Do New Century Catalysts Unravel the Mechanism of Stereocontrol of Old Ziegler—Natta Catalysts?, Accounts of Chemical Research, 2004, vol. 37, No. 4, pp. 231-241.

(56) References Cited

OTHER PUBLICATIONS

Demetgul, Cahit et al., Synthesis and characterization of a Schiff base derived from 2-aminobenzylamine and its Cu(II) complex: electropolymerization of the complex on a platinum electrode, Journal of Coordination Chemistry, 2010, vol. 63, No. 12, pp. 2181-2191.
Egami, Hiromichi et al., Fe(salan)-Catalyzed Asymmetric Oxidation of Sulfides with Hydrogen Peroxide in Water, 2007, J. Am. Chem. Soc., vol. 129, pp. 8940-8941.
Egami, Hiromichi et al., Nb(salan)-Catalyzed Asymmetric Epoxidation of Allylic Alcohols with Hydrogen Peroxide, 2008, J. Am. Chem. Soc., vol. 47, pp. 5171-5174.
Egami, Hiromichi et al., Oxidation Catalysis of Nb(Salan) Complexes: Asymmetric Epoxidation of Allylic Alcohols Using Aqueous Hydrogen Peroxide as an Oxidant, 2010, J. Am. Chem. Soc., vol. 132, pp. 5886-5895.
Egami, Hiromichi et al., Enantioenriched Synthesis of C1-Symmetric BINOLs: Iron-Catalyzed Cross-Coupling of 2-Naphthols and Some Mechanistic Insight, 2010, J. Am. Chem. Soc., vol. 132, pp. 13633-13635.
Gendler, Shimrit, et al., Titanium and Zirconium Complexes of Robust Salophan Ligands. Coordination Chemistry and Olefin Polymerization Catalysis, J. Am. Chem. Soc., 2008, vol. 130, pp. 2144-2145.
Groysman, Stanislav et al., Salophan Complexes of Group IV Metals, Eur. J. Inorg. Chem. 2005, pp. 2480-2485.
Kondo, Shoichi et al., A μ-Oxo-μ-η2 :η2-Peroxo Titanium Complex as a Reservoir of Active Species in Asymmetric Epoxidation Using Hydrogen Peroxide, 2008, Angew. Chem. Int. Ed., vol. 47, pp. 10195-10198.
Lamberti, Marina et al., Mechanism of stereospecific polymerization of α-olefins by late-transition metal and octahedral group 4 metal catalysts, Coord. Chem. Rev. vol. 253, 2009, pp. 2082-2097.
Leflon, P. et al., Determination of aluminum in bone in haemodialyzed patients, using inductively coupled argon plasma emission spectrometry, Clinica Chimica Acta, 1990, vol. 191, issues 1-2, pp. 31-38.
Manna, Cesar M. et al., Markedly different cytotoxicity of the two enantiomers of C2-symmetrical Ti(IV) phenolato complexes; mechanistic implications, 2010, Dalton Trans., vol. 39, pp. 1182-1184.
Matsumoto, Kazuhiro et al., Asymmetric catalysis of metal complexes with non-planar ONNO ligands: salen, salalen and salan, Chem. Commun., 2007, pp. 3619-3627.
Matsumoto, Kazuhiro et al., Asymmetric epoxidation of olefins catalyzed by Ti(salan) complexes using aqueous hydrogen peroxide as the oxidant, 2008, Pure and Applied Chemistry, vol. 80, pp. 1071-1077.
Matsumoto, Kazuhiro et al., Highly Enantioselective Epoxidation of Styrenes Catalyzed by Proline-Derived C1-Symmetric Titanium(Salan) Complexes, Angew. Chem. Int. Ed. 2009, vol. 48, pp. 7432-7435.
Meker, Sigalit. et al., Major impact of N-methylation on cytotoxicity and hydrolysis of salan Ti(IV) complexes: sterics and electronics are intertwined, 2011, Dalton Trans., vol. 40, pp. 9802-9809.
Nakano, Koji et al., Alternating Copolymerization of Cyclohexene Oxide with Carbon Dioxide Catalyzed by (salalen) CrCl Complexes, Macromelecules, 2009, vol. 42, pp. 6972-6980.
Press, Konstantin et al., Salalen Titanium Complexes in the Highly Isospecific Polymerization of 1-Hexene and Propylene, Angew. Chem., Int. Ed., 2011, vol. 50, pp. 3529-3532.
Press, Konstantin et al., Zirconium and hafnium Salalen complexes in isospecific polymerisation of propylene, Dalton Trans., 2013, vol. 42, pp. 9096-9103.
Sawada, Yuji, et al., Titanium-Salan-Catalyzed Asymmetric Epoxidation with Aqueous Hydrogen Peroxide as the Oxidant, Angew. Chem. Int. Ed., 2006, vol. 45, pp. 3478-3480.
Segal, Sharon et al., Isospecific Polymerization of Vinylcyclohexane by Zirconium Complexes of Salan Ligands, Macromolecules, 2008, vol. 41, No. 5, pp. 1612-1617.
Segal, Sharon et al., Zirconium and Titanium Diamine Bis(phenolate) Catalysts for α-Olefin Polymerization: From Atactic Oligo(1-hexene) to Ultrahigh-Molecular-Weight Isotactic Poly(1-hexene), Organomellics, 2005, vol. 24, No. 2, pp. 200-202.
Sergeeva, Ekaterina et al., Salan ligands assembled around chiral bipyrrolidine: predetermination of chirality around octahedral Ti and Zr centres, Chem. Commun, 2009, pp. 3053-3055.
Sergeeva, Ekaterina et al., 2,2'-Bipyrrolidine versus 1,2-Diaminocyclohexane as Chiral Cores for Helically Wrapping Diamine—Diolate Ligands, Inorganic Chemistry, 2009, vol. 48, No. 17, pp. 8075-8077.
Seyforth, Dietmar, Alkyl and Aryl Derivatives of the Alkali Metals: Strong Bases and Reactive Nucleophiles. 2. Wilhelm Schlenk's Organoalkali-Metal Chemistry. The Metal Displacement and the Transmetalation Reactions. Metalation of Weakly Acidic Hydrocarbons. Superbases, Organometallics, 2009, vol. 28, pp. 2-33.
Stopper, Ayellet et al., Ring-Opening Polymerization of Lactide with Zr Complexes of {ONSO} Ligands: From Heterotactically Inclined to Isotactically Inclined Poly(lactic acid), Macromolecules, 2012, vol. 45, pp. 698-704.
Strianese M., et al., A Comparative Study on the Polymerization of α-Olefins Catalyzed by Salen and Salan Zirconium ComplexesMacromol. Chem. Phys. 2008, vol. 209, pp. 585-592.
Talarico, Giovanni et al., Origin of the Regiochemistry of Propene Insertion at Octahedral col. 4 Polymerization Catalysts: Design or Serendipity?, J. Am. Chem. Soc., 2003, vol. 125, pp. 7172-7173.
Tshuva, Edit Y. et al., Isospecific Living Polymerization of 1-Hexene by a Readily Available Nonmetallocene C2-Symmetrical Zirconium Catalyst, J. Am. Chem. Soc., 2000, vol. 122, pp. 10706-10707.
Yeori et al., Salalen: A hybrid Salan/Salen tetradentate [ONNO]-type ligand and its coordination behavior with group IV metals, Inorg. Chem. Commun., vol. 7, 2004, pp. 280-282.
Yeori, Adi et al., Diastereoisomerically Selective Enantiomerically Pure Titanium Complexes of Salan Ligands: Synthesis, Structure, and Preliminary Activity Studies, Inorganic Chemistry, 2005, vol. 44, No. 13, pp. 4466-4468.
Yeori, Adi et al., Diastereomerically-Specific Zirconium Complexes of Chiral Salan Ligands: Isospecific Polymerization of 1-Hexene and 4-Methyl-1-pentene and Cyclopolymerization of 1,5-Hexadiene, J . Am. Chem. Soc, 2006, vol. 128, pp. 13062-13063.
Yeori, Adi et al., Cyclopolymerization of 1,5-Hexadiene by Enantiomerically-Pure Zirconium Salan Complexes. Polymer Optical Activity Reveals α-Olefin Face Preference, Macromolecules, 2007, vol. 40, No. 24, pp. 8521-8523.
Zucchini, U. et al., Synthesis and Properties of Some Titanium and Zirconium Benzyl Derivatives, J. Organomet. Chem., 1971, vol. 26, pp. 357-372.
PCT/US2013/046538 International Search Report and Written Opinion, Nov. 8, 2013.
PCT/US2013/046582 International Search Report and Written Opinion, Nov. 5, 2013.
PCT/US2013/046601 International Search Report and Written Opinion, Nov. 13, 2013.
Busico et al. "Living Ziegler-Natta Polymerization: True or False?", Macromolecules Symposium, 226: 1-16, 2005.
Busico et al. "Reactivity of Secondary Metal-Alkyls in Catalytic Propene Polymerization: How Dormant Are 'Dormant Chains'?", Journal of the American Chemical Society, 127(6): 1608-1609, 2005.
Ciancaleone et al. "Activation of a Bis(Phenoxy-Amine) Precatalyst for Olefin Polymerization: First Evidence for an Outer Sphere Ion Pair With the Methylborate Counterion", Dalton Transactions, p. 8824-8827, 2009.
Ciancaleone et al. "Stucture-Activity Relationship in Olefin Polymerization Catalysis: Is Entropy the Key?", Journal of the American Chemical Society, JACS, 132: 13651-13653, 2010.
Tshuva et al. "Single-Step Synthesis of Salans and Substituted Salans by Mannich Condensation", Tetrahedron Letters, 42: 6405-6407, 2001.
Official Action Dated Sep. 6, 2013 From the US Patent and Trademark Office Re. U.S. Appl. No. 13/805,011.
Restriction Official Action Dated May 13, 2013 From the US Patent and Trademark Office Re. U.S. Appl. No. 13/805,011.
Notice of Allowance Dated Jul. 1, 2014 From the US Patent and Trademark Office Re. U.S. Appl. No. 13/805,011.

(56) References Cited

OTHER PUBLICATIONS

Communication Pursuant to Article 94(3) EPC Dated Mar. 14, 2014 From the European Patent Office Re. Application No. 11736169.1.
Communication Relating to the Results of the Partial International Search Dated Apr. 19, 2012 From the International Searching Authority Re. Application No. PCT/IB2012/050267.
Corrected International Search Report and the Written Opinion Dated Sep. 25, 2012 From the International Searching Authority Re. Application No. PCT/IB2012/050267.
International Search Report and the Written Opinion Dated Jun. 19, 2012 From the International Searching Authority Re. Application No. PCT/IB2012/050267.
Office Action Dated Jul. 28, 2014 From the State Intellectual Property Office of the People's Republic of China Re. Application No. 201180039237.5.
Search Report Dated Jul. 28, 2014 From the State Intellectual Property Office of the People's Republic of China Re. Application No. 201180039237.5.
International Preliminary Report and the Written Opinion on Patentability Dated Jan. 3, 2013 From the International Bureau of WIPO Re. Application No. PCT/IL2011/000482.
International Search Report Dated Dec. 5, 2011 From the International Searching Authority Re. Application No. PCT/IL2011/000482.
International Preliminary Report and Written Opinion on Patentability Dated Jul. 23, 2013 From the International Bureau of WIPO Re. Application No. PCT/IB2012/050267.
Office Action Dated Jul. 28, 2014 From the State Intellectual Property Office of the People's Republic of China Re. Application No. 201180039237.5 Translation Into English.
PCT/US2014/041362—ISR and WO, Oct. 1, 2014.
PCT/US2014/039786—ISR and WO, Sep. 29, 2014.
PCT/US2014/039766—ISR and WO, Oct. 31, 2014.
Immel et al., Cytotoxic dinuclear titanium-salan complexes: Structural and biological characterization, Journal of Inorganic Biochemistry, 2012, vol. 106, pp. 68-75.
Sanz et al. "Monocyclopentadienyl Bis(phenoxo-imino) Zirconium Complexes as Precatalyst Species for Olefin Polymerization. Stereospecific Methylation of an Imino Group with Formation of a Zirconium-amido Bond", Organometallics, 23: 5324-5331, 2004.

* cited by examiner

SALENOL CATALYST

RELATED APPLICATION

This application claims priority to and the benefit of provisional application U.S. 61/837,588 filed Jun. 20, 2013, which is incorporated by reference herein in its entirety.

FIELD OF THE INVENTION

This invention relates to catalyst compounds and catalyst systems comprising such, methods of preparing such, uses thereof and products obtained thereby.

BACKGROUND OF THE INVENTION

Olefin polymerization catalysts are of great use in industry. Hence there is interest in finding new catalyst systems that increase the commercial usefulness of the catalyst and allow the production of polymers having improved properties.

There is a need in the art for new and improved catalysts and catalyst systems to obtain new and improved polyolefins, polymerization processes, and the like. Accordingly, there is a need in the art for new and improved catalyst systems for the polymerization of olefins for one or more of the following purposes: to achieve one or more specific polymer properties, such as high polymer melting point and/or high polymer molecular weights; to increase conversion or comonomer incorporation; and/or to alter comonomer distribution without deterioration of the properties of the resulting polymer.

SUMMARY OF THE INVENTION

The instant disclosure is directed to catalyst compounds, catalyst systems comprising such compounds, processes for the preparation of the catalyst compounds and systems, processes for the polymerization of olefins using such catalyst compounds and systems and the polyolefins obtained from such processes. In an embodiment according to the invention, the catalyst compound comprises Group 3, 4, 5 and/or 6 disubstituted compounds supported by a tetradentate salenol ligand system coordinated with the metal.

The invention relates to a catalyst compound represented by the formula:

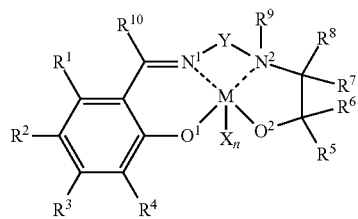

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1, R^2, R^3, R^4, R^5, R^6, R^7, R^8, R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

This invention also relates to catalyst systems comprising such compounds, processes for the preparation of the catalyst compounds and systems, processes for the polymerization of olefins using such catalyst compounds and systems and the polyolefins obtained from such processes.

DETAILED DESCRIPTION

Figure 1:
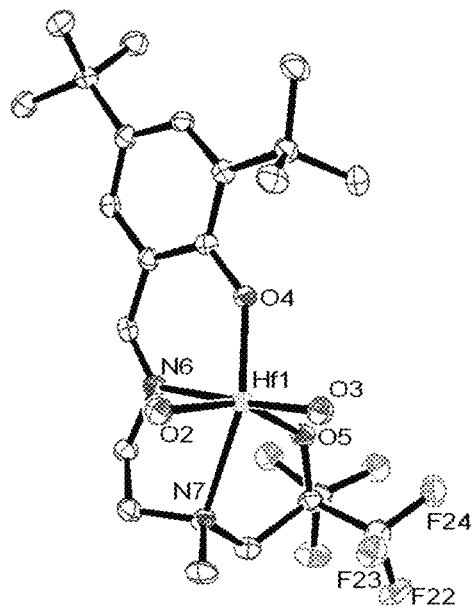
FIG. 1 is a representation of molecular structure as determined by single crystal X-ray diffraction according to the inventive embodiment of Example A-Hf(O-tert-Bu)$_2$.

For the purposes of this invention and the claims thereto, the new numbering scheme for the Periodic Table Groups is used as described in Chem. Eng. News, 1985, 63, 27. Therefore, a "Group 4 metal" is an element from Group 4 of the Periodic Table, e.g., Hf, Ti or Zr.

In the structures depicted throughout this specification and the claims, a solid line indicates a bond, and each dashed line represents a bond having varying degrees of covalency and a varying degree of coordination.

The terms "hydrocarbyl radical," "hydrocarbyl" and "hydrocarbyl group" are used interchangeably throughout this document unless otherwise specified. For purposes of this disclosure, a hydrocarbyl radical is defined to be $C_1$ to $C_{70}$ radicals, or $C_1$ to $C_{20}$ radicals, or $C_1$ to $C_{10}$ radicals, or $C_6$ to $C_{70}$ radicals, or $C_6$ to $C_{20}$ radicals, or $C_7$ to $C_{20}$ radicals that may be linear, branched, or cyclic where appropriate (aromatic or non-aromatic); and includes hydrocarbyl radicals substituted with other hydrocarbyl radicals and/or one or more functional groups comprising elements from Groups 13-17 of the periodic table of the elements. In addition two or more such hydrocarbyl radicals may together form a fused ring system, including partially or fully hydrogenated fused ring systems, which may include heterocyclic radicals.

The term "substituted" means that a hydrogen atom and/or a carbon atom in the base structure has been replaced with a hydrocarbyl radical, and/or a functional group, and/or a heteroatom or a heteroatom containing group. Accordingly, the term hydrocarbyl radical includes heteroatom containing groups. For purposes herein, a heteroatom is defined as any atom other than carbon and hydrogen. For example, methyl cyclopentadiene (Cp) is a Cp group, which is the base structure, substituted with a methyl radical, which may also be referred to as a methyl functional group, ethyl alcohol is an ethyl group, which is the base structure, substituted with an —OH functional group, and pyridine is a phenyl group having a carbon in the base structure of the benzene ring substituted with a nitrogen atom.

For purposes herein, a hydrocarbyl radical may be independently selected from substituted or unsubstituted methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl.

For purposes herein, hydrocarbyl radicals may also include isomers of saturated, partially unsaturated and aromatic cyclic structures wherein the radical may additionally be subjected to the types of substitutions described above. The term "aryl", "aryl radical", and/or "aryl group" refers to aromatic cyclic structures, which may be substituted with hydrocarbyl radicals and/or functional groups as defined herein. Examples of aryl radicals include: acenaphthenyl, acenaphthylenyl, acridinyl, anthracenyl, benzanthracenyl, benzimidazolyl, benzisoxazolyl, benzofluoranthenyl, benzofuranyl, benzoperylenyl, benzopyrenyl, benzothiazolyl, benzothiophenyl, benzoxazolyl, benzyl, carbazolyl, carbolinyl, chrysenyl, cinnolinyl, coronenyl, cyclohexyl, cyclohexenyl, methylcyclohexyl, dibenzoanthracenyl, fluoranthenyl, fluorenyl, furanyl, imidazolyl, indazolyl, indenopyrenyl, indolyl, indolinyl, isobenzofuranyl, isoindolyl, isoquinolinyl, isoxazolyl, methyl benzyl, methylphenyl, naphthyl, oxazolyl, phenanthrenyl, phenyl, purinyl, pyrazinyl, pyrazolyl, pyrenyl, pyridazinyl, pyridinyl, pyrimidinyl, pyrrolyl, quinazolinyl, quinolonyl, quinoxalinyl, thiazolyl, thiophenyl, and the like.

It is to be understood that for purposes herein, when a radical is listed, it indicates that the base structure of the radical (the radical type) and all other radicals formed when that radical is subjected to the substitutions defined above. Alkyl, alkenyl, and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and nevopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (and cyclobutenyls and cyclopropenyls). Cyclic compounds having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Likewise the terms "functional group", "group" and "substituent" are also used interchangeably throughout this document unless otherwise specified. For purposes herein, a functional group includes both organic and inorganic radicals and moieties comprising elements from Groups 13, 14, 15, 16, and 17 of the periodic table of elements. Suitable functional groups may include hydrocarbyl radicals, e.g., alkyl radicals, alkene radicals, aryl radicals, and/or halogen (Cl, Br, I, F), O, S, Se, Te, $NR^*_x$, $OR^*$, $SeR^*$, $TeR^*$, $PR^*_x$, $AsR^*_x$, $SbR^*_x$, $SR^*$, $BR^*_x$, $SiR^*_x$, $GeR^*_x$, $SnR^*_x$, $PbR^*_x$, and/or the like, wherein $R^*$ is a $C_1$ to $C_{20}$ hydrocarbyl as defined above and wherein x is the appropriate integer to provide an electron neutral moiety. Other examples of functional groups include those typically referred to as amines, imides, amides, ethers, alcohols (hydroxides), sulfides, sulfates, phosphides, halides, phosphonates, alkoxides, esters, carboxylates, aldehydes, and the like.

For purposes herein "direct bonds," "direct covalent bonds" or "directly bridged" are used interchangeably to refer to covalent bonds directly between atoms that do not have any intervening atoms.

For purposes herein an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer.

For purposes herein a "polymer" has two or more of the same or different "mer" units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An oligomer is typically a polymer having a low molecular weight, such as an Mn of less than 25,000 g/mol, or in an embodiment according to the invention less than 2,500 g/mol, or a low number of mer units, such as 75 mer units or less. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this disclosure, the term "α-olefin" includes $C_2$-$C_{22}$ olefins. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

The terms "catalyst", "catalyst compound", and "transition metal compound" are defined to mean a compound capable of initiating polymerization catalysis under the appropriate conditions. In the description herein, the catalyst may be described as a catalyst precursor, a pre-catalyst compound, or a transition metal compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. A "catalyst system" is combination of at least one catalyst compound, at least one activator, an optional co-activator, and an optional support material, where the system can polymerize monomers to polymer. For the purposes of this invention and the claims thereto, when catalyst systems are described as comprising neutral stable forms of the components it is well understood by one of ordinary skill in the art that the ionic form of the component is the form that reacts with the monomers to produce polymers.

For purposes herein the term "catalyst productivity" is a measure of how many grams of polymer (P) are produced using a polymerization catalyst comprising W g of catalyst (cat), over a period of time of T hours; and may be expressed by the following formula: P/(T×W) and expressed in units of gPgcat$^{-1}$hr$^{-1}$. Conversion is the amount of monomer that is converted to polymer product, and is reported as mol % and is calculated based on the polymer yield and the amount of monomer fed into the reactor. Catalyst activity is a measure of how active the catalyst is and is reported as the mass of product polymer (P) produced per mole of catalyst (cat) used (kg P/mol cat).

An "anionic ligand" is a negatively charged ligand which donates one or more pairs of electrons to a metal ion. A "neutral donor ligand" is a neutrally charged ligand which donates one or more pairs of electrons to a metal ion.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In an embodiment according to the invention a co-activator can be pre-mixed with the catalyst compound to form an alkylated catalyst compound.

As used herein, Mn is number average molecular weight as determined by proton nuclear magnetic resonance spectroscopy ($^1$H NMR) unless stated otherwise, Mw is weight average molecular weight determined by gel permeation chromatography (GPC), and Mz is z average molecular weight determined by GPC, wt % is weight percent, and mol % is mole percent. Molecular weight distribution (MWD) is defined to be Mw divided by Mn. Unless otherwise noted, all molecular weight units, e.g., Mw, Mn, Mz, are reported in g/mol.

The following abbreviations may be used through this specification: Me is methyl, Ph is phenyl, Et is ethyl, Pr is propyl, iPr is isopropyl, n-Pr is normal propyl, Bu is butyl, iso-butyl is isobutyl, sec-butyl refers to secondary butyl, tert-butyl, t-butyl, tert-Bu, or t-Bu refers to tertiary butyl, n-butyl is normal butyl, pMe is para-methyl, Bn is benzyl, THF is tetrahydrofuran, Mes is mesityl, also known as 1,3,5-trimethylbenzene, Tol is toluene, TMS is trimethylsilyl, TIBAL is triisobutylaluminum, TNOAL is triisobutyl n-octylaluminum, MAO is methylalumoxane, MOMO is methoxymethoxy (also referred to as methoxymethyl ether), N is nitrogen (including that $N^a$, $N^b$, $N^1$, $N^2$ are nitrogen) and O is oxygen (including that $O^a$, $O^b$, $O^1$, $O^2$ are oxygen). Further, $N^a$ and $N^1$, $N^2$ and $N^b$, $O^a$ and $O^1$, and $O^b$ and $O^2$ are equivalent and may be used interchangeably between formulae.

For purposes herein whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

For purposes herein, RT is room temperature, which is defined as 25° C. unless otherwise specified. All percentages are weight percent (wt %) unless otherwise specified.

In the description herein, the salenol catalyst may be described as a catalyst precursor, a pre-catalyst compound, salenol catalyst compound, bridged salenol catalyst compound or a transition metal compound, and these terms are used interchangeably.

Polypropylene microstructure is determined by $^{13}$C-NMR spectroscopy, including the concentration of isotactic and syndiotactic dyads ([m] and [r]), triads ([mm] and [rr]), and pentads ([mmmm] and [rrrr]). The designation "m" or "r" describes the stereochemistry of pairs of contiguous propylene groups, "m" referring to meso and "r" to racemic. Samples are dissolved in d$_2$-1,1,2,2-tetrachloroethane, and spectra recorded at 125° C. using a 100 MHz (or higher) NMR spectrometer. Polymer resonance peaks are referenced to mmmm=21.8 ppm. Calculations involved in the characterization of polymers by NMR are described by F. A. Bovey in Polymer Conformation and Configuration (Academic Press, New York 1969) and J. Randall in Polymer Sequence Determination, $^{13}$C-NMR Method (Academic Press, New York, 1977).

Melting point (Tm or Tmelt), also referred to as melting temperature, and heat of fusion (Hf) of polymers are determined using differential scanning calorimetry (DSC) on a commercially available instrument (e.g., TA Instruments 2920 DSC). Typically, 6 to 10 mg of molded polymer or plasticized polymer are sealed in an aluminum pan and loaded into the instrument at room temperature. Melting data (first heat) is acquired by heating the sample to at least 30° C. above its melting temperature, typically 220° C. for polypropylene, at a heating rate of 10° C./min. The sample is held for at least 5 minutes at this temperature to destroy its thermal history. Crystallization data are acquired by cooling the sample from the melt to at least 50° C. below the crystallization temperature, typically −50° C. for polypropylene, at a cooling rate of 20° C./min. The sample is held at this temperature for at least 5 minutes, and finally heated at 10° C./min to acquire additional melting data (second heat). The endothermic melting transition (first and second heat) and exothermic crystallization transition are analyzed according to standard procedures. The melting temperatures reported are the peak melting temperatures from the second heat unless otherwise specified.

For polymers displaying multiple peaks, the melting temperature is defined to be the peak melting temperature from the melting trace associated with the largest endothermic calorimetric response (as opposed to the peak occurring at the highest temperature). Areas under the DSC curve are used to determine the heat of transition (heat of fusion, $H_f$, upon melting), which can be used to calculate the degree of crystallinity (also called the percent crystallinity). The percent crystallinity (X %) is calculated using the formula: [area under the curve (in J/g)/H° (in J/g)]*100, where H° is the ideal heat of fusion for a perfect crystal of the homopolymer of the major monomer component. These values for H° are to be obtained from the *Polymer Handbook, Fourth Edition*, published by John Wiley and Sons, New York 1999, except that a value of 290 J/g is used for H° (polyethylene), a value of 140 J/g is used for H° (polybutene), and a value of 207 J/g is used for H° (polypropylene).

For purposes herein, a chiral carbon is indicated by a C* and/or at least two of the substituents are indicated using the flying wedge and dotted wedge depictions known in the art. For purposes herein, unless otherwise specified, a structure comprising a chiral carbon, whether expressly indicated or not, includes the enantiomerically pure compound or compounds in the case of multiple chiral carbons, the racemic mixture of compounds, or a combination thereof, including racemic mixtures combined with enantiomerically pure isomers in the case of multiple chiral carbons present in the same molecule.

For purposes herein, a bulky ligand substitution on a salenol catalyst compound is defined as a $C_4$ to $C_{20}$ hydrocarbyl radical; —$SR^a$, —$NR^a_2$ and —$PR^a_2$, where each $R^a$ is independently a $C_4$ to $C_{20}$ hydrocarbyl; or a $C_4$ to $C_{20}$ hydrocarbyl substituted organometalloid. The molecular volume of a substituent is used herein as an approximation of spatial steric bulk. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple 'Back of the Envelope' Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: MV=8.3 Vs, where Vs is the scaled volume, which is the sum of the relative volumes of the constituent atoms, and is calculated from the molecular formula of the substituent using the following table of relative volumes. For fused rings, the Vs is decreased by 7.5% per fused ring.

| Element | Relative Volume, Å (Vs) |
| --- | --- |
| H | 1 |
| 1st short period, Li to F | 2 |
| 2nd short period, Na to Cl | 4 |
| 1st long period, K to Br | 5 |
| 2nd long period, Rb to I | 7.5 |
| 3rd long period, Cs to Bi | 9 |

For purposes herein, a bulky substituent is defined as any substituent having a molecular volume greater than or equal to a tertiary-butyl substitution (MV=8.3 Vs=141.1). Examples of other suitable bulky substituents include adamantyl, halo substituted and unsubstituted aryl functional groups, and the like.

For purposes herein, a salenol catalyst compound refers to a non-symmetric tetradentate ligand system comprising an imine group bound to a phenol arm and an amine group bound to an alcoholate arm bridged to the phenol arm, coordinated with a metal. The salenol ligand system includes [$O^a,N^a,N^b,O^b$] where $O^a$ and $N^a$ are attached to the first arm of the ligand comprising the imine-phenolate moiety and $N^b$ and $O^b$ are attached to the second arm of the ligand comprising the alcoholate moiety (O=oxygen and N=nitrogen). The first and second arms of the ligand are attached to each other by a bridge moiety Y between $N^a$ and $N^b$. Each of $O^a$, $N^a$, $N^b$, and $O^b$ are coordinated with the metal atom. For purposes herein a bridged salenol catalyst compound has one of the general structures I or II:

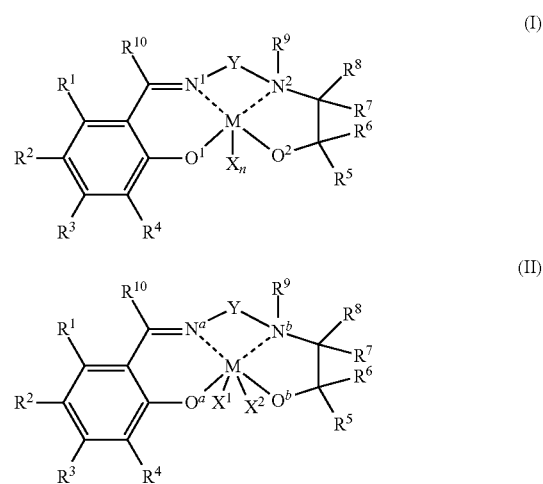

wherein each solid line represents a covalent bond and each dashed line represents a bond having varying degrees of covalency and a varying degree of coordination and where $R^1$ to $R^{10}$, M, n, X, $X^1$, $X^2$ and Y are as described below.

For purposes herein, a "fac" (facial) configuration refers to a bridged salenol ligand structure (II) where $O^a$ and/or $O^b$ is not in the [$N^a,N^b$,M] plane in a six-coordinated arrangement centered around the metal atom, or stated differently, all three of the atoms [$O^a,N^a,N^b$] and/or all three of the atoms [$N^a,N^b,O^b$] are on the same side ([$O^a,N^b$] and [$N^a,O^b$] are located cis); whereas in a "mer" (meridional) configuration, $O^a$ and/or $O^b$ are in the [$N^a,N^b$,M] plane, or stated differently, $O^a$ is on the opposite side of the metal center (located trans) with respect to $N^b$ and/or $O^b$ is on the opposite side of the metal center or trans with respect to $N^a$. For purposes herein, in the binary wrapping mode designations, the configuration of [$O^a,N^a,N^b$] is stated first and [$N^a,N^b,O^b$] second, e.g., "fac-mer" refers to fac [$O^a,N^a,N^b$] and mer [$N^a,N^b,O^b$].

The four arrangements of the $O^a$—$N^a$—$N^b$—$O^b$ salenol catalyst compounds which are possible are: mer-mer, also referred to in the art as trans with respect to the labile groups $X^1$ and $X^2$; fac-fac, also referred to in the art as cis-alpha; and fac-mer and mer-fac, both of which are generally referred to as cis-beta, but which are actually different isomers as illustrated below.

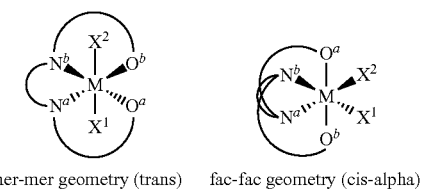

mer-mer geometry (trans)    fac-fac geometry (cis-alpha)

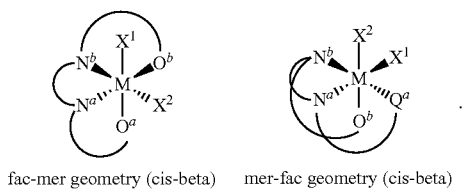

fac-mer geometry (cis-beta)   mer-fac geometry (cis-beta)

Catalyst Compounds

In an embodiment according to the invention, the catalyst comprises Group 3, 4, 5 and/or 6 dialkyl compounds supported by a tetradentate di-anionic salenol ligand, which, in embodiments of the invention, is useful to polymerize olefins and/or α-olefins to produce polyolefins and/or poly(α-olefins).

In an embodiment according to the invention, the catalyst compounds are represented by the formula:

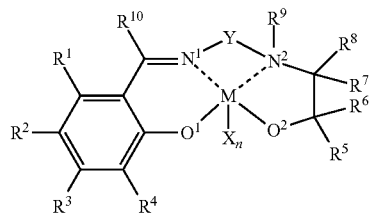

(I)

wherein each solid line represents a covalent bond and each dashed line represents a bond having varying degrees of covalency and a varying degree of coordination;

wherein M is a Group 3, 4, 5 or 6 transition metal;

wherein $N^1$ and $N^2$ are nitrogen and $O^1$ and $O^2$ are oxygen;

wherein n is 1 or 2;

wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;

wherein Y is selected from the group consisting of divalent $C_1$ to $C_{20}$ hydrocarbyl radicals, divalent functional groups comprising elements from Groups 13-17 of the periodic table of the elements, and combinations thereof; and wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

In a particular embodiment according to the invention, the catalyst compounds are represented by the formula:

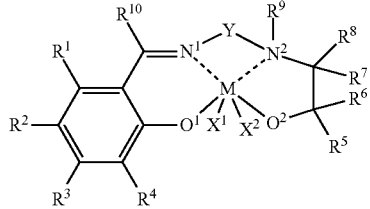

(II)

wherein each solid line represents a covalent bond and each dashed line represents a bond having varying degrees of covalency and a varying degree of coordination;

wherein M is a Group 4, 5 or 6 transition metal;

wherein $N^1$ and $N^2$ are nitrogen and $O^1$ and $O^2$ are oxygen;

wherein each of $X^1$ and $X^2$ is, independently, a univalent $C_1$ to $C_{20}$ hydrocarbyl radical, a functional group comprising elements from Groups 13-17 of the periodic table of the elements, or $X^1$ and $X^2$ join together to form a $C_4$ to $C_{62}$ cyclic or polycyclic ring structure;

wherein Y is selected from the group consisting of divalent $C_1$ to $C_{20}$ hydrocarbyl radicals, divalent functional groups comprising elements from Groups 13-17 of the periodic table of the elements, and combinations thereof; and wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

In an embodiment according to the invention, the catalyst compound comprises $[O^1,N^1,N^2]$—$[N^1,N^2,O^2]$ in a fac-mer, a mer-fac, or a fac-fac arrangement.

According to a particular embodiment of the invention, M is Ti, Hf or Zr. In an embodiment according to the invention, $X^1$ and $X^2$ are each a benzyl radical. In a preferred embodiment of the invention, M is Hf, Ti or Zr and $X^1$ and $X^2$ are each a benzyl radical.

In an embodiment according to the invention, each of $R^1$, $R^2$, $R^3$, $R^4$, $R^5$, $R^6$, $R^7$, $R^8$, $R^9$, and $R^{10}$ is, independently, hydrogen, a halogen, or a $C_1$ to $C_{30}$ hydrocarbyl radical.

In an embodiment according to the invention, each of $R^1$, $R^2$, $R^3$, $R^4$, $R^5$, $R^6$, $R^7$, $R^8$, $R^9$, and $R^{10}$ is, independently, hydrogen, a halogen, or a $C_1$ to $C_{10}$ hydrocarbyl radical.

According to a particular embodiment of the invention, Y comprises a phenylene divalent radical.

According to a particular embodiment according to the invention, Y and $R^9$ join together to form a $C_4$ to $C_{62}$ cyclic or polycyclic ring structure, represented by one of the formulae:

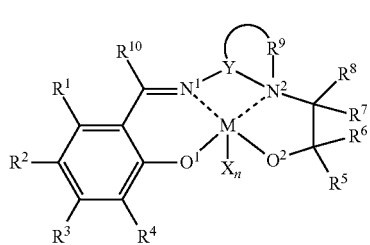

(III)

-continued

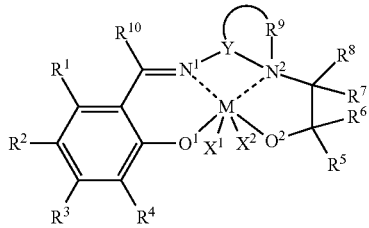
(IV)

wherein M, $O^1$, $O^2$, $N^1$, $N^2$, X, $X^1$, $X^2$, Y and $R^1$ to $R^8$ and $R^{10}$ are as previously defined.

In a particular embodiment according to the invention:
each of X or $X^1$ and $X^2$ are benzyl radicals;
at least one of $R^2$, $R^4$, $R^5$, $R^6$ and $R^9$ is independently selected from the group consisting of: $C_1$-$C_{10}$ alkyl, $C_1$-$C_{10}$ cycloalkyl, $C_1$-$C_{10}$ alkenyl, $C_1$-$C_{10}$ alkoxy, aryl substituted $C_1$-$C_{10}$ alkyl, $C_1$-$C_{10}$ aryl, halo and combinations thereof; and
$R^1$, $R^3$, $R^7$, $R^8$ and $R^{19}$ are hydrogen.

In a particular embodiment according to the invention, at least one of $R^2$, $R^4$, $R^5$, $R^6$ and $R^9$ is independently selected from the group consisting of: methyl, ethyl, isopropyl, isobutyl, tertiary-butyl, isopentyl, 2-methyl-2-phenylethyl; methoxy, benzyl, adamantyl, chloro, bromo, iodo and combinations thereof.

In a particular embodiment according to the invention, $R^2$, $R^4$, or a combination thereof is chloro, bromo, iodo, a bulky ligand substitution, or a combination thereof, the bulky ligand substitution comprises a molecular volume greater than or equal to the molecular volume of a tertiary-butyl substitution; and the bulky ligand substitution comprises a $C_4$ to $C_{20}$ hydrocarbyl radical, $—SR^a$, $—NR^a_2$, $—PR^a_2$ or combination thereof, where $R^a$ is independently a $C_4$ to $C_{20}$ hydrocarbyl.

In a particular embodiment according to the invention, $R^4$ is a bulky ligand substitution comprising a $C_4$ to $C_{20}$ hydrocarbyl radical and $R^2$ is chloro, bromo, or iodo.

In an embodiment according to the invention $R^5$ and $R^6$ comprise aryl hydrocarbyl groups, in a particular embodiment according to the invention, $R^5$ and $R^6$ comprise 2-napthyl hydrocarbyl groups.

In a particular embodiment according to the invention, the catalyst compound is represented by one of the formulae:

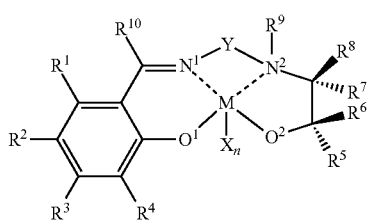
(V)

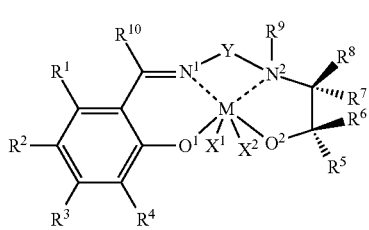
(VI)

wherein M, $O^1$, $O^2$, $N^1$, $N^2$, X, $X^1$, $X^2$, Y and $R^1$ to $R^{19}$ are as previously defined, and wherein $R^5$ is different than $R^6$; $R^7$ is different than $R^8$, or a combination thereof. In another particular embodiment according to the invention, the catalyst is an enantiomerically pure isomer with respect to at least one chiral carbon.

In an embodiment according to the invention, a catalyst system comprises an activator and a catalyst compound represented by represented by one of the formulae:

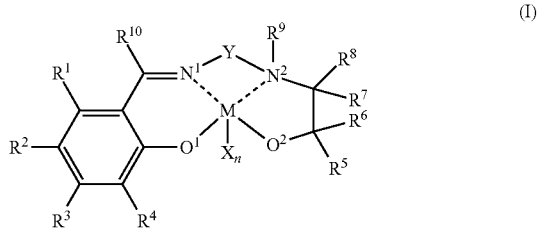
(I)

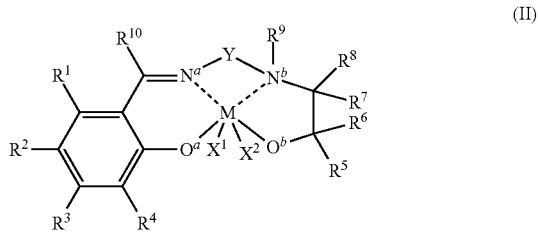
(II)

wherein M, $O^1$, $O^2$, $N^1$, $N^2$, X, $X^1$, $X^2$, Y and $R^1$ to $R^{10}$ are as previously defined.

In a particular embodiment according to the invention, the catalyst system comprises $[O^1,N^1,N^2]$—$[N^1,N^2,O^2]$ in a fac-mer, a mer-fac, or a fac-fac arrangement; or wherein activation rearranges $[O^1,N^1,N^2]$—$[N^1,N^2,O^2]$ into a fac-mer arrangement or a mer-fac arrangement. In other embodiments of the invention, the catalyst system comprises $[O^1,N^1,N^2]$—$[N^1,N^2,O^2]$ in a fac-fac arrangement; or wherein activation rearranges $[O^1,N^1,N^2]$—$[N^1,N^2,O^2]$ into a fac-fac arrangement.

In an embodiment according to the invention, the activator comprises alumoxane, a non-coordinating anion activator or a combination thereof. In a particular embodiment according to the invention, the activator comprises alumoxane and the alumoxane is present at a ratio of 1 mole aluminum or more per mole of catalyst compound.

In a particular embodiment according to the invention, the activator is represented by the formula: $(Z)_d^+(A^{d-})$
wherein Z is (L-H), or a reducible Lewis Acid, wherein L is a neutral Lewis base, H is hydrogen and $(L-H)^+$ is a Bronsted acid;
$A^{d-}$ is a non-coordinating anion having the charge $d^-$; and
d is an integer from 1 to 3.

In an embodiment according to the invention, the activator is represented by the formula: $(Z)_d^+(A^{d-})$
wherein $A^{d-}$ is a non-coordinating anion having the charge $d^-$;
d is an integer from 1 to 3, and
Z is a reducible Lewis acid represented by the formula: $(Ar_3C^+)$, where Ar is aryl radical, an aryl radical substituted with a heteroatom, an aryl radical substituted with one or more $C_1$ to $C_{40}$ hydrocarbyl radicals, an aryl radical substituted with one or more functional groups comprising elements from Groups 13-17 of the periodic table of the elements, or a combination thereof.

In an embodiment according to the invention, a process to activate a catalyst system comprises combining an activator with a catalyst compound represented by one of the formulae:

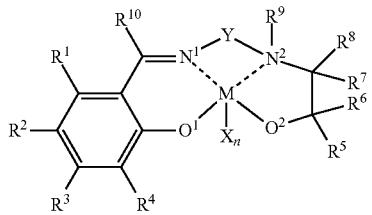
(I)

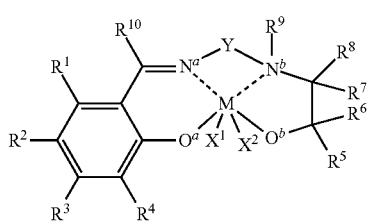
(II)

wherein M, $O^1$, $O^2$, $N^1$, $N^2$, X, $X^1$, $X^2$, Y and $R^1$ to $R^{10}$ are as previously defined.

In a particular embodiment according to the invention, the catalyst compound of the process comprises $[O^1,N^1,N^2]$—$[N^1,N^2,O^2]$ in a fac-mer, a mer-fac, or a fac-fac arrangement; or wherein activation rearranges $[O^1,N^1,N^2]$—$[N^1,N^2,O^2]$ into a fac-mer arrangement or a mer-fac arrangement or a fac-fac arrangement.

Methods to Prepare the Catalyst Compounds.

In an embodiment according to the invention, the salenol ligand may be prepared by imine condensation of a diamine bridge compound $NH_2$—Y—NR'''H with an aldehyde located ortho to a hydroxy functional group, e.g., a substituted salicylaldehyde base structure, to form an imine-Y-bridged-amine (Reaction A), followed by reaction of the resultant imine-Y-bridged-amine with an epoxide to produce the salenol ligand (Reaction B).

The salenol ligand is then converted into the metal di-substituted catalyst precursor by reaction with a substituted metal compound, also referred to as a "metalating agent", to yield the finished complex. In an embodiment according to the invention, the salenol ligand is converted into the metal substituted catalyst precursor by reaction with a metalation reagent $MX_{(n+2)}$ where n is 1 or 2, e.g., a metal tri- or tetra-substituted compound to yield the finished complex (reaction C1) or into the metal di-substituted catalyst precursor by reaction with a metalation reagent $MX_4$, e.g., a metal tetra-substituted compound to yield the finished complex (reaction C2).

Reaction A:

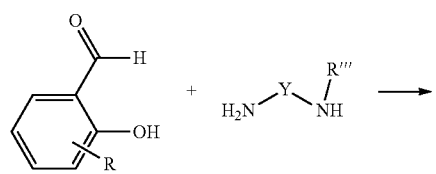

Reaction B:

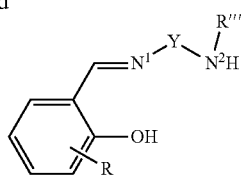

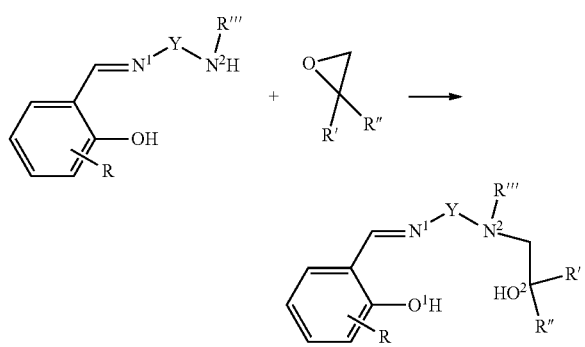

Reaction C1:

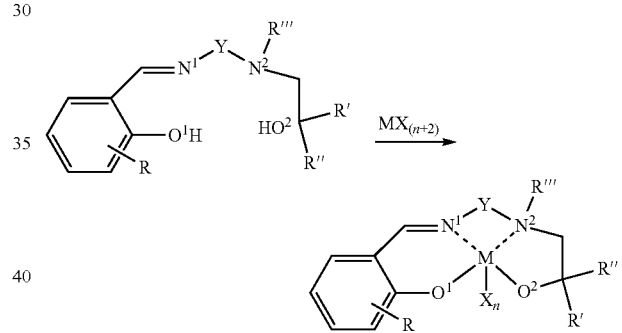

Reaction C2:

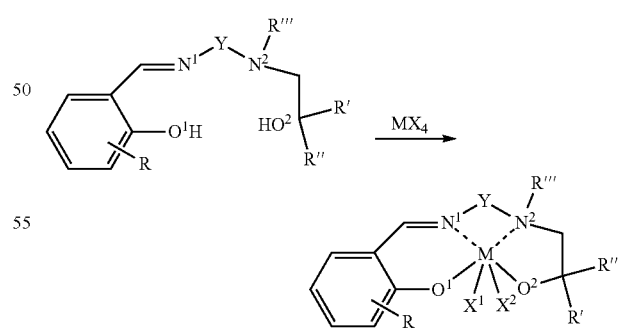

In embodiments according to the invention, the salenol ligand may be contacted with the metalation reagent in Reaction C1 or in Reaction C2 to form the catalyst compound prior to combination with the activator, and subsequently the catalyst compound may be contacted with the activator, with or without isolation of the precursor catalyst compound; or the salenol ligand and the metalation reagent may be contacted in Reaction C1 or in Reaction C2 in the presence of the activator, in the presence of one or more olefins, or a combination thereof, e.g., in an in situ metalation, activation and/or polymerization process.

Activators

The terms "cocatalyst" and "activator" are used interchangeably to describe activators and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Activators may include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

In one embodiment of the invention, alumoxane activators are utilized as an activator in the catalyst composition. Alumoxanes are generally oligomeric compounds containing —Al($R^1$)—O— sub-units, where $R^1$ is an alkyl radical. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the catalyst precursor compound comprises an abstractable ligand which is an alkyl, halide, alkoxide or amide. Mixtures of different alumoxanes and modified alumoxanes may also be used. In an embodiment according to the invention, visually clear methylalumoxane may be used. A cloudy or gelled alumoxane can be filtered to produce a clear solution or clear alumoxane can be decanted from the cloudy solution. A useful alumoxane is a modified methyl alumoxane (MMAO) described in U.S. Pat. No. 5,041,584 and/or commercially available from Akzo Chemicals, Inc. under the trade designation Modified Methylalumoxane type 3A.

When the activator is an alumoxane (modified or unmodified), in an embodiment according to the invention, the maximum amount of activator is typically present at a 5000-fold molar excess Al/M over the catalyst compound (per metal catalytic site). In an embodiment according to the invention, the minimum activator-to-catalyst-compound, which is determined according to molar concentration of the transition metal M, in an embodiment according to the inventions is 1 mole aluminum or less to mole of transition metal M. In an embodiment according to the invention, the activator comprises alumoxane and the alumoxane is present at a ratio of 1 mole aluminum or more to mole of catalyst compound. In an embodiment according to the invention, the minimum activator-to-catalyst-compound molar ratio is a 1:1 molar ratio. Other embodiments of Al:M ranges include from 1:1 to 500:1, or from 1:1 to 200:1, or from 1:1 to 100:1, or from 1:1 to 50:1.

In an embodiment according to the invention, little or no alumoxane (i.e., less than 0.001 wt %) is used in the polymerization processes described herein. In an embodiment according to the invention, alumoxane is present at 0.00 mole %, or the alumoxane is present at a molar ratio of aluminum to catalyst compound transition metal less than 500:1, or less than 300:1, or less than 100:1, or less than 1:1.

The term "non-coordinating anion" (NCA) refers to an anion which either does not coordinate to a cation, or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible with the polymerization or catalyst system, stabilize the transition metal cation in the sense of balancing its ionic charge at +1, and yet are sufficiently labile to permit displacement during polymerization.

In an embodiment according to the invention, an ionizing or stoichiometric activator may be used, which may be neutral or ionic, such as tri(n-butyl)ammonium boron metalloid precursor, polyhalogenated heteroborane anions (WO 98/43983), boric acid (U.S. Pat. No. 5,942,459), or a combination thereof. In an embodiment according to the invention, neutral or ionic activators alone or in combination with alumoxane or modified alumoxane activators may be used.

Examples of neutral stoichiometric activators include tri-substituted boron, tellurium, aluminum, gallium, and indium, or mixtures thereof. The three substituent groups or radicals can be the same or different and in an embodiment according to the invention are each independently selected from substituted or unsubstituted alkyls, alkenyls, alkyns, aryls, alkoxy, and halogens. In an embodiment according to the invention, the three groups are independently selected from halogen, mono or multicyclic (including halosubstituted) aryls, alkyls, and alkenyl compounds, and mixtures thereof; or independently selected from alkenyl radicals having 1 to 20 carbon atoms, alkyl radicals having 1 to 20 carbon atoms, alkoxy radicals having 1 to 20 carbon atoms and aryl or substituted aryl radicals having 3 to 20 carbon atoms. In an embodiment according to the invention, the three substituent groups are alkyl radicals having 1 to 20 carbon atoms, phenyl, naphthyl, or mixtures thereof. In an embodiment according to the invention, the three groups are halogenated aryl groups, e.g., fluorinated aryl groups. In an embodiment according to the invention the neutral stoichiometric activator is tris perfluorophenyl boron or tris perfluoronaphthyl boron.

In an embodiment according to the invention, ionic stoichiometric activator compounds may include an active proton, or some other cation associated with, but not coordinated to, or only loosely coordinated to the remaining ion of the ionizing compound. Suitable examples include compounds and the like described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198, 401; 5,066,741; 5,206,197; 5,241,025; 5,384,299; 5,502,124; and WO 1996/04319; all of which are herein fully incorporated by reference.

In an embodiment according to the invention compounds useful as an activator comprise a cation, which is, for example, a Bronsted acid capable of donating a proton, and a compatible non-coordinating anion which anion is relatively large (bulky), capable of stabilizing the active catalyst species (the Group 4 cation, e.g.) which is formed when the two compounds are combined and said anion will be sufficiently labile to be displaced by olefinic, diolefinic or acetylenically unsaturated substrates or other neutral Lewis bases, such as ethers, amines, and the like. Two classes of useful compatible non-coordinating anions are disclosed in EP 0 277 003 A1, and EP 0 277 004 A1, which include anionic coordination complexes comprising a plurality of lipophilic radicals covalently coordinated to and shielding a central charge-bearing metal or metalloid core; and anions comprising a plurality of boron atoms such as carboranes, metallacarboranes, and boranes.

In an embodiment according to the invention, the stoichiometric activators include a cation and an anion component, and may be represented by the following formula (1):

$$(Z)_d^+ (A^{d-}) \quad (1)$$

wherein Z is (L-H) or a reducible Lewis Acid, L is a neutral Lewis base; H is hydrogen; (L-H)$^+$ is a Bronsted acid; A$^{d-}$ is a non-coordinating anion having the charge d−; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the catalyst precursor, resulting in a cationic transition metal species, or the activating cation (L-H)$_d^+$ is a Bronsted acid, capable of donating a proton to the catalyst precursor resulting in a transition metal cation, including ammoniums, oxoniums, phosphoniums, silyliums, and mixtures thereof, or ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it may be represented by the formula: (Ar$_3$C$^+$), where Ar is aryl or aryl substituted with a heteroatom, or a C$_1$ to C$_{40}$ hydrocarbyl, the reducible Lewis acid may be represented by the formula: (Ph$_3$C$^+$), where Ph is phenyl or phenyl substituted with a heteroatom, and/or a C$_1$ to C$_{40}$ hydrocarbyl. In an embodiment according to the invention, the reducible Lewis acid is triphenyl carbenium.

Embodiments according to the invention of the anion component A$^{d-}$ include those having the formula [M$^{k+}$Q$_n$]$^{d-}$ wherein k is 1, 2, or 3; n is 1, 2, 3, 4, 5 or 6, or 3, 4, 5 or 6; n−k=d; M is an element selected from Group 13 of the Periodic Table of the Elements, or boron or aluminum, and Q is independently a hydride, bridged or unbridged dialkylamido, halide, alkoxide, aryloxide, hydrocarbyl radicals, said Q having up to 20 carbon atoms with the proviso that in not more than one occurrence is Q a halide, and two Q groups may form a ring structure. Each Q may be a fluorinated hydrocarbyl radical having 1 to 20 carbon atoms, or each Q is a fluorinated aryl radical, or each Q is a pentafluoryl aryl radical. Examples of suitable A$^{d-}$ components also include diboron compounds as disclosed in U.S. Pat. No. 5,447,895, which is fully incorporated herein by reference.

In an embodiment according to the invention, this invention relates to a method to polymerize olefins comprising contacting olefins (e.g., ethylene and/or propylene) with a salenol catalyst compound, an optional chain transfer agent (CTA) and a boron containing NCA activator represented by the formula (1) where: Z is (L-H) or a reducible Lewis acid; L is an neutral Lewis base (as further described above); H is hydrogen; (L-H) is a Bronsted acid (as further described above); A$^{d-}$ is a boron containing non-coordinating anion having the charged (as further described above); d is 1, 2, or 3.

In an embodiment according to the invention in any of the NCA's represented by Formula 1 described above, the anion component A$^{d-}$ is represented by the formula [M*$^{k*+}$Q*$_{n*}$]$^{d*-}$ wherein k* is 1, 2, or 3; n* is 1, 2, 3, 4, 5, or 6 (or 1, 2, 3, or 4); n*−k*=d*; M* is boron; and Q* is independently selected from hydride, bridged or unbridged dialkylamido, halogen, alkoxide, aryloxide, hydrocarbyl radicals, said Q* having up to 20 carbon atoms with the proviso that in not more than 1 occurrence is Q* a halogen.

This invention also relates to a method to polymerize olefins comprising contacting olefins (such as ethylene and/or propylene) with a salenol catalyst compound as described above, optionally with a CTA and an NCA activator represented by the Formula (2):

$$R_n M^{**}(ArNHal)_{4-n} \quad (2)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula 2 also comprises a suitable cation that is essentially non-interfering with the ionic catalyst complexes formed with the transition metal compounds, or the cation is Z$_d^+$ as described above.

In an embodiment according to the invention in any of the NCA's comprising an anion represented by Formula 2 described above, R is selected from the group consisting of C$_1$ to C$_{30}$ hydrocarbyl radicals. In an embodiment according to the invention, C$_1$ to C$_{30}$ hydrocarbyl radicals may be substituted with one or more C$_1$ to C$_{20}$ hydrocarbyl radicals, halide, hydrocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means C$_4$ to C$_{20}$ hydrocarbyl radicals; —SR$^a$, —NR$^a_2$, and —PR$^a_2$, where each R$^a$ is independently a C$_4$ to C$_{20}$ hydrocarbyl as defined above; or a C$_4$ to C$_{20}$ hydrocarbyl substituted organometalloid.

In an embodiment according to the invention in any of the NCA's comprising an anion represented by Formula 2 described above, the NCA also comprises cation comprising a reducible Lewis acid represented by the formula: (Ar$_3$C$^+$), where Ar is aryl or aryl substituted with a heteroatom, and/or a C$_1$ to C$_{40}$ hydrocarbyl, or the reducible Lewis acid represented by the formula: (Ph$_3$C$^+$), where Ph is phenyl or phenyl substituted with one or more heteroatoms, and/or C$_1$ to C$_{40}$ hydrocarbyls.

In an embodiment according to the invention in any of the NCA's comprising an anion represented by Formula 2 described above, the NCA may also comprise a cation represented by the formula, (L-H)$_d^+$, wherein L is an neutral Lewis base; H is hydrogen; (L-H) is a Bronsted acid; and d is 1, 2, or 3, or (L-H)$_d^+$ is a Bronsted acid selected from ammoniums, oxoniums, phosphoniums, silyliums, and mixtures thereof.

Further examples of useful activators include those disclosed in U.S. Pat. No. 7,297,653 and U.S. Pat. No. 7,799,879, which are fully incorporated by reference herein.

In an embodiment according to the invention, an activator useful herein comprises a salt of a cationic oxidizing agent and a noncoordinating, compatible anion represented by the Formula (3):

$$(OX^{e+})_d (A^{d-})_e \quad (3)$$

wherein OX$^{e+}$ is a cationic oxidizing agent having a charge of e+; e is 1, 2, or 3; d is 1, 2 or 3; and A$^{d-}$ is a non-coordinating anion having the charge of d− (as further described above). Examples of cationic oxidizing agents include: ferrocenium, hydrocarbyl-substituted ferrocenium, Ag$^+$, or Pb$^{+2}$. Suitable embodiments of A$^{d-}$ include tetrakis(pentafluorophenyl)borate.

In an embodiment according to the invention, the salenol catalyst compounds, optional CTA's, and/or NCA's described herein can be used with bulky activators. A "bulky activator" as used herein refers to anionic activators represented by the formula:

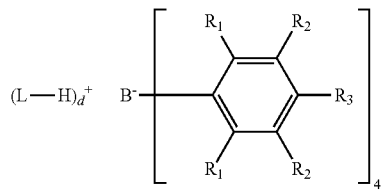

where each $R_1$ is, independently, a halide, or a fluoride;
each $R_2$ is, independently, a halide, a $C_6$ to $C_{20}$ substituted aromatic hydrocarbyl radical or a siloxy group of the formula —O—Si—$R_a$, where $R_a$ is a $C_1$ to $C_{20}$ hydrocarbyl or hydrocarbylsilyl radical (or $R_2$ is a fluoride or a perfluorinated phenyl radical);
each $R_3$ is a halide, $C_6$ to $C_{20}$ substituted aromatic hydrocarbyl radical or a siloxy group of the formula —O—Si—$R_a$, where $R_a$ is a $C_1$ to $C_{20}$ hydrocarbyl radical or hydrocarbylsilyl group (or $R_3$ is a fluoride or a $C_6$ perfluorinated aromatic hydrocarbyl radical); wherein $R_2$ and $R_3$ can form one or more saturated or unsaturated, substituted or unsubstituted rings (or $R_2$ and $R_3$ form a perfluorinated phenyl ring);

L is an neutral Lewis base; $(L-H)^+$ is a Bronsted acid; d is 1, 2, or 3;
wherein the anion has a molecular weight of greater than 1020 g/mol; and
wherein at least three of the substituents on the B atom each have a molecular volume of greater than 250 cubic Å, or greater than 300 cubic Å, or greater than 500 cubic Å.

As discussed above, "Molecular volume" is used herein as an approximation of spatial steric bulk of an activator molecule in solution. Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | MV Per subst. (Å³) | Total MV (Å³) |
|---|---|---|---|---|
| Dimethylanilinium tetrakis(perfluoronaphthyl)borate | | $C_{10}F_7$ | 261 | 1044 |
| Dimethylanilinium tetrakis(perfluorobiphenyl)borate | | $C_{12}F_9$ | 349 | 1396 |
| [4-tButyl-PhNMe₂H] [($(C_6F_3(C_6F_5)_2)_4B$)] | | $C_{18}F_{13}$ | 515 | 2060 |

Exemplary bulky activators useful in catalyst systems herein include: trimethylammonium tetrakis(perfluoronaphthyl)borate, triethylammonium tetrakis(perfluoronaphthyl) borate, tripropylammonium tetrakis(perfluoronaphthyl)borate, tri(n-butyl)ammonium tetrakis(perfluoronaphthyl) borate, tri(tert-butyl)ammonium tetrakis(perfluoronaphthyl) borate, N,N-dimethylanilinium tetrakis(perfluoronaphthyl) borate, N,N-diethylanilinium tetrakis(perfluoronaphthyl) borate, N,N-dimethyl-(2,4,6-trimethylanilinium)tetrakis (perfluoronaphthyl)borate, tropillium tetrakis (perfluoronaphthyl)borate, triphenylcarbenium tetrakis (perfluoronaphthyl)borate, triphenylphosphonium tetrakis (perfluoronaphthyl)borate, triethylsilylium tetrakis (perfluoronaphthyl)borate, benzene(diazonium)tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(tert-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene (diazonium)tetrakis (perfluorobiphenyl)borate, [4-tert-butyl-PhNMe$_2$H][(C$_6$F$_3$(C$_6$F$_5$)$_2$)$_4$B], and the types disclosed in U.S. Pat. No. 7,297,653, which is fully incorporated by reference herein.

Illustrative, but not limiting, examples of boron compounds which may be used as an activator in the processes according to the instant disclosure include: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenyl borate, triphenylcarbenium tetraphenylborate, triphenylphosphonium tetraphenyl borate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylaniliniumtetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, tropillium tetrakis (pentafluorophenyl)borate, triphenylcarbenium tetrakis (pentafluorophenyl)borate, triphenylphosphonium tetrakis (pentafluorophenyl)borate, triethylsilylium tetrakis (pentafluorophenyl)borate, benzene(diazonium)tetrakis (pentafluorophenyl)borate, trimethylammonium tetrakis-(2,3,4,6-tetrafluorophenyl)borate, triethyl ammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethyl anilinium tetrakis-(2,3,4,6-tetrafluorophenyl)borate, N,N-dimethyl-(2,4,6-trimethyl anilinium)tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluoro phenyl)borate, triethyl silylium tetrakis-(2,3,4,6-tetrafluorophenyl)borate, benzene(diazonium)tetrakis-(2,3,4,6-tetrafluorophenyl)borate, trimethylammonium tetrakis (perfluoro naphthyl)borate, triethylammonium tetrakis (perfluoronaphthyl)borate, tripropyl ammonium tetrakis (perfluoronaphthyl)borate, tri(n-butyl)ammonium tetrakis (perfluoronaphthyl)borate, tri(tert-butyl)ammonium tetrakis (perfluoronaphthyl)borate, N,N-dimethyl anilinium tetrakis (perfluoronaphthyl)borate, N,N-diethyl anilinium tetrakis (perfluoronaphthyl)borate, N,N-dimethyl-(2,4,6-trimethyl anilinium)tetrakis(perfluoronaphthyl)borate, tropilliumtetrakis(perfluoronaphthyl)borate, triphenylcarbenium tetrakis (perfluoronaphthyl)borate, triphenylphosphonium tetrakis (perfluoronaphthyl)borate, triethylsilylium tetrakis (perfluoronaphthyl)borate, benzene(diazonium)tetrakis (perfluoronaphthyl)borate, trimethylammonium tetrakis (perfluorobiphenyl)borate, triethylammoniumtetrakis (perfluorobiphenyl)borate, tripropylammonium tetrakis (perfluorobiphenyl)borate, tri(n-butyl)ammonium tetrakis (perfluorobiphenyl)borate, tri(tert-butyl)ammonium tetrakis (perfluorobiphenyl)borate, N,N-dimethylanilinium tetrakis (perfluorobiphenyl)borate, N,N-diethyl aniliniumtetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis (perfluorobiphenyl)borate, trimethylammonium tetrakis(3,5-bis(trifluoromethyl)phenyl)borate, triethylammoniumtetrakis(3,5-bis(trifluoro methyl)phenyl) borate, tripropylammoniumtetrakis(3,5-bis(trifluoromethyl) phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethyl aniliniumtetrakis(3,5-bis(trifluoromethyl)phenyl)borate, N,N-diethylanilinium tetrakis(3,5-bis(trifluoromethyl) phenyl)borate, N,N-dimethyl-(2,4,6-trimethylanilinium) tetrakis(3,5-bis(trifluoromethyl)phenyl)borate, tropillium tetrakis(3,5-bis(trifluoro methyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, benzene(diazonium)tetrakis(3,5-bis(trifluoromethyl)phenyl)borate, and dialkyl ammonium salts, such as: di-(i-propyl)ammonium tetrakis(pentafluorophenyl)borate, and dicyclohexyl ammonium tetrakis(pentafluorophenyl)borate; and additional tri-substituted phosphonium salts, such as tri(o-tolyl)phosphonium tetrakis(pentafluorophenyl) borate, and tri(2,6-dimethylphenyl)phosphonium tetrakis (pentafluorophenyl)borate.

Suitable activators include: N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoro methyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, triphenylcarbenium tetrakis(perfluorophenyl)borate, [Ph$_3$C$^+$][B(C$_6$F$_5$)$_4^-$], [Me$_3$NH$^+$][B(C$_6$F$_5$)$_4^-$]; 1-(4-(tris(pentafluorophenyl)borate)-2,3,5,6-tetrafluorophenyl)pyrrolidinium; tetrakis(pentafluorophenyl)borate; and 4-(tris(pentafluorophenyl)borate)-2,3,5,6-tetrafluoropyridine.

In an embodiment according to the invention, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluoro phenyl)borate, triphenylcarbenium tetrakis(perfluoronaphthyl)borate, triphenyl carbenium tetrakis (perfluorobiphenyl)borate, triphenylcarbenium tetrakis(3,5-bis(trifluoromethyl)phenyl)borate).

In an embodiment according to the invention, the activator comprises one or more of: trialkylammonium tetrakis(pentafluorophenyl)borate, N,N-dialkylanilinium tetrakis(pentafluorophenyl)borate, N,N-dimethyl-(2,4,6-trimethylanilinium)tetrakis(pentafluorophenyl)borate, trialkylammonium tetrakis-(2,3,4,6-tetrafluoro phenyl)borate, N,N-dialkylanilinium tetrakis-(2,3,4,6-tetrafluorophenyl)borate, trialkylammonium tetrakis(perfluoronaphthyl) borate, N,N-dialkylanilinium tetrakis(perfluoronaphthyl) borate, trialkylammonium tetrakis(perfluorobiphenyl)borate, N,N-dialkylanilinium tetrakis(perfluorobiphenyl)borate, trialkylammoniumtetrakis(3,5-bis(trifluoromethyl)phenyl)borate, N,N-dialkyl aniliniumtetrakis(3,5-bis(trifluoromethyl) phenyl)borate, N,N-dialkyl-(2,4,6-trimethyl anilinium) tetrakis(3,5-bis(trifluoromethyl)phenyl)borate, di-(i-propyl) ammonium tetrakis(pentafluorophenyl)borate, where alkyl is methyl, ethyl, propyl, n-butyl, sec-butyl, or tert-butyl.

In an embodiment according to the invention, any of the activators described herein may be mixed together before or after combination with the catalyst compound and/or optional CTA and/or NCA, or before being mixed with the catalyst compound and/or optional CTA, and/or NCA.

In an embodiment according to the invention two NCA activators may be used in the polymerization and the molar ratio of the first NCA activator to the second NCA activator can be any ratio. In an embodiment according to the invention, the molar ratio of the first NCA activator to the second NCA activator is 0.01:1 to 10,000:1, or 0.1:1 to 1000:1, or 1:1 to 100:1.

In an embodiment according to the invention, the NCA activator-to-catalyst ratio is a 1:1 molar ratio, or 0.1:1 to 100:1, or 0.5:1 to 200:1, or 1:1 to 500:1 or 1:1 to 1000:1. In an embodiment according to the invention, the NCA activator-to-catalyst ratio is 0.5:1 to 10:1, or 1:1 to 5:1.

In an embodiment according to the invention, the catalyst compounds can be combined with combinations of alumoxanes and NCA's (see for example, U.S. Pat. No. 5,153,157, U.S. Pat. No. 5,453,410, EP 0 573 120 B1, WO 94/07928, and WO 95/14044 which discuss the use of an alumoxane in combination with an ionizing activator, all of which are incorporated by reference herein).

Useful chain transfer agents are typically alkylalumoxanes, a compound represented by the formula $AlR_3$, $ZnR_2$ (where each R is, independently, a $C_1$-$C_8$ aliphatic radical, preferably methyl, ethyl, propyl butyl, penyl, hexyl octyl or an isomer thereof) or a combination thereof, such as diethyl zinc, methylalumoxane, trimethylaluminum, triisobutylaluminum, trioctylaluminum, or a combination thereof.

Scavengers or Co-Activators

In an embodiment according to the invention the catalyst system may further include scavengers and/or co-activators. Suitable aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum and the like. Other oxophilic species such as diethyl zinc may be used.

Catalyst Supports

In an embodiment according to the invention, the catalyst system may comprise an inert support material. In an embodiment according to the invention, the support material comprises a porous support material, for example, talc, and/or inorganic oxides. Other suitable support materials include zeolites, clays, organoclays, or any other organic or inorganic support material and the like, or mixtures thereof.

In an embodiment according to the invention, the support material is an inorganic oxide in a finely divided form. Suitable inorganic oxide materials for use in catalyst systems herein include Groups 2, 4, 13, and 14 metal oxides, such as silica, alumina, and mixtures thereof. Other inorganic oxides that may be employed either alone or in combination with the silica, and/or alumina include magnesia, titania, zirconia, montmorillonite, phyllosilicate, and/or the like. Other suitable support materials include finely divided functionalized polyolefins, such as finely divided polyethylene.

In an embodiment according to the invention, the support material may have a surface area in the range of from about 10 to about 700 $m^2/g$, pore volume in the range of from about 0.1 to about 4.0 cc/g and average particle size in the range of from about 5 to about 500 µm, or the surface area of the support material is in the range of from about 50 to about 500 $m^2/g$, pore volume of from about 0.5 to about 3.5 cc/g and average particle size of from about 10 to about 200 µm. In an embodiment according to the invention, a majority portion of the surface area of the support material is in the range is from about 100 to about 400 $m^2/g$, pore volume from about 0.8 to about 3.0 cc/g and average particle size is from about 5 to about 100 µm. In an embodiment according to the invention, the average pore size of the support material is in the range of from 10 to 1000 Å, or 50 to about 500 Å, or 75 to about 350 Å. In an embodiment according to the invention, the support material is a high surface area, amorphous silica having a surface area greater than or equal to about 300 $m^2/g$, and/or a pore volume of 1.65 $cm^3/g$. Suitable silicas are marketed under the tradenames of Davison 952 or Davison 955 by the Davison Chemical Division of W.R. Grace and Company. In an embodiment according to the invention the support may comprise Davison 948.

In an embodiment according to the invention, the support material should be essentially dry, that is, essentially free of absorbed water. Drying of the support material can be effected by heating or calcining at about 100° C. to about 1000° C., or at a temperature of at least about 400° C., or 500° C., or 600° C. When the support material is silica, it is heated to at least 200° C., or about 200° C. to about 850° C., or at least 600° C. for a time of about 1 minute to about 100 hours, or from about 12 hours to about 72 hours, or from about 24 hours to about 60 hours. In an embodiment according to the invention, the calcined support material must have at least some reactive hydroxyl (OH) groups to produce supported catalyst systems according to the instant disclosure.

In an embodiment according to the invention, the calcined support material is contacted with at least one polymerization catalyst comprising at least one catalyst compound and an activator. In an embodiment according to the invention, the support material, having reactive surface groups, typically hydroxyl groups, is slurried in a non-polar solvent and the resulting slurry is contacted with a solution of a catalyst compound and an activator. In an embodiment according to the invention, the slurry of the support material is first contacted with the activator for a period of time in the range of from about 0.5 hours to about 24 hours, or from about 2 hours to about 16 hours, or from about 4 hours to about 8 hours. The solution of the catalyst compound is then contacted with the isolated support/activator. In an embodiment according to the invention, the supported catalyst system is generated in situ. In alternate embodiment, the slurry of the support material is first contacted with the catalyst compound for a period of time in the range of from about 0.5 hours to about 24 hours, or from about 2 hours to about 16 hours, or from about 4 hours to about 8 hours. The slurry of the supported catalyst compound is then contacted with the activator solution.

In an embodiment according to the invention, the mixture of the catalyst, activator and support is heated to about 0° C. to about 70° C., or to about 23° C. to about 60° C., or to 25° C. (room temperature). Contact times typically range from about 0.5 hours to about 24 hours, or from about 2 hours to about 16 hours, or from about 4 hours to about 8 hours.

Suitable non-polar solvents are materials in which all of the reactants used herein, i.e., the activator and the catalyst compound are at least partially soluble and which are liquid at reaction temperatures. Suitable non-polar solvents include alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In an embodiment according to the invention, a polymerization process includes contacting monomers (such as ethylene and propylene), and optionally comonomers, with a catalyst system comprising an activator and at least one catalyst compound, as described above. In an embodiment according to the invention, the catalyst compound and activator may be combined in any order, and may be combined prior to contacting with the monomer. In an embodiment according to the invention, the catalyst compound and/or the activator are combined after contacting with the monomer.

In an embodiment according to the invention, a process to polymerize olefins comprises contacting one or more olefins with a catalyst system at polymerization conditions to produce a polyolefin, the catalyst system comprising an activator and a catalyst compound represented by one of the formula:

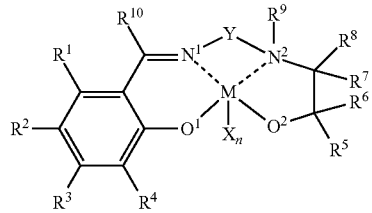

(I)

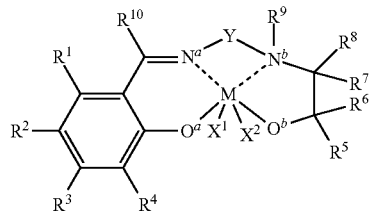

(II)

wherein M, $O^1$, $O^2$, $N^1$, $N^2$, X, $X^1$, $X^2$, Y and $R^1$ to $R^{10}$ are as previously defined.

In a particular embodiment according to the invention the process comprises a catalyst compound comprising $[O^1,N^1,N^2]$—$[N^1,N^2,O^2]$ in a fac-mer, a mer-fac, or a fac-fac arrangement; or wherein activation rearranges $[O^1,N^1,N^2]$—$[N^1,N^2,O^2]$ into a fac-mer arrangement or a mer-fac arrangement. In other process embodiments according to the invention, the catalyst compound comprises $[O^1,N^1,N^2]$—$[N^1N^2,O^2]$ in a fac-fac arrangement; or wherein activation rearranges $[O^1,N^1,N^2]$—$[N^1,N^2,O^2]$ into a fac-fac arrangement.

In an embodiment according to the invention, the salenol ligand may be combined with the metalation reagent to produce the metal di-substituted catalyst precursor prior to catalyst activation, with or without isolation of the catalyst precursor, or simultaneously with activation and/or in the presence of monomers such that the catalyst is formed in-situ during the polymerization process. In an embodiment according to the invention, a process to polymerize olefins may comprise:

contacting a salenol ligand with a metalation reagent to produce a catalyst precursor; and contacting the catalyst precursor with an activator and one or more olefins at polymerization conditions to produce a polyolefin;

wherein the salenol ligand is represented by the formula:

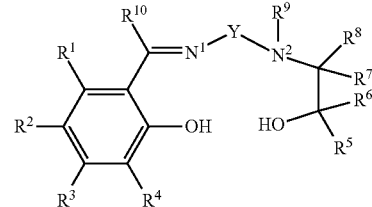

wherein the metalation reagent is represented by the formula: $MX^1X^2X^3X^4$ wherein the catalyst precursor is represented by the formula:

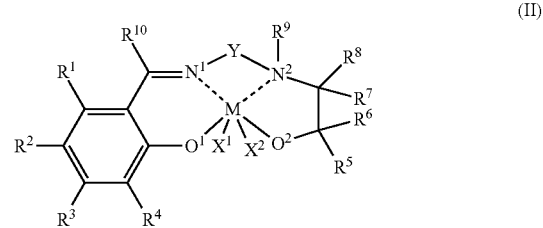

(II)

wherein each solid line represents a covalent bond and each dashed line represents a bond having varying degrees of covalency and a varying degree of coordination;

wherein M is a Group 3, 4, 5 or 6 transition metal;

wherein $N^1$ and $N^2$ are nitrogen and $O^1$ and $O^2$ are oxygen;

wherein each of $X^1$, $X^2$, $X^3$ and $X^4$ is, independently, a univalent $C_1$ to $C_{20}$ hydrocarbyl radical, a functional group comprising elements from Groups 13-17 of the periodic table of the elements, or $X^1$ and $X^2$ may join together to form a $C_4$ to $C_{62}$ cyclic or polycyclic ring structure, provided however where M is trivalent $X^2$ is not present;

wherein Y is selected from the group consisting of divalent $C_1$ to $C_{20}$ hydrocarbyl radicals, divalent functional groups comprising elements from Groups 13-17 of the periodic table of the elements, and combinations thereof; and wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

In an embodiment according to the invention, the salenol ligand and the metalation reagent may be contacted prior to combination with the activator and subsequently with the activator without isolation of the catalyst precursor, or simultaneously with activation and/or in the presence of monomers such that the catalyst is formed in-situ during the polymerization process. In an embodiment according to the invention, the salenol ligand and the metalation reagent may be contacted in the presence of the activator, in the presence of one or more olefins, or a combination thereof, e.g., in an in-situ polymerization process.

In an embodiment according to the invention, the polymerization conditions comprise a temperature of from about 0° C. to about 300° C., a pressure from about 0.35 MPa to about 10 MPa, and a time from about 0.1 minutes to about 24 hours.

In an embodiment according to the invention, one or more olefins comprise propylene.

In a particular embodiment, the polyolefin comprises at least 50 mole % propylene, preferably at least 75 mol % propylene, preferably at least 85 mol % propylene.

In an embodiment according to the invention, two or more different catalyst compounds are present in the catalyst system used herein. In an embodiment according to the invention, two or more different catalyst compounds are present in the reaction zone where the process(es) described herein occur. When two transition metal compound based catalysts are used in one reactor as a mixed catalyst system, the two transition metal compounds are chosen such that the two are preferably compatible. Compatible catalysts are those catalysts having similar kinetics of termination and insertion of monomer and comonomer(s) and/or do not detrimentally interact with each other. For purposes herein, the term "incompatible catalysts" refers to and means catalysts that satisfy one or more of the following:

1) those catalysts that when present together reduce the activity of at least one of the catalysts by greater than 50%;

2) those catalysts that under the same reactive conditions produce polymers such that one of the polymers has a molecular weight that is more than twice the molecular weight of the other polymer; and 3) those catalysts that differ in comonomer incorporation or reactivity ratio under the same conditions by more than about 30%. A simple screening method such as by $^{1}$H or $^{13}$C NMR, known to those of ordinary skill in the art, can be used to determine which transition metal compounds are compatible. In an embodiment according to the invention, the catalyst systems use the same activator for the catalyst compounds. In an embodiment according to the invention, two or more different activators, such as a non-coordinating anion activator and an alumoxane, can be used in combination. If one or more catalyst compounds contain an $X^1$ or $X^2$ ligand which is not a hydride, or a hydrocarbyl, then in an embodiment according to the invention the alumoxane is contacted with the catalyst compounds prior to addition of the non-coordinating anion activator.

In an embodiment according to the invention, when two transition metal compounds (pre-catalysts) are utilized, they may be used in any ratio. In an embodiment according to the invention, a molar ratio of a first transition metal compound (A) to a second transition metal compound (B) will fall within the range of (A:B) 1:1000 to 1000:1, or 1:100 to 500:1, or 1:10 to 200:1, or 1:1 to 100:1, or 1:1 to 75:1, or 5:1 to 50:1. The particular ratio chosen will depend on the exact pre-catalysts chosen, the method of activation, and the end product desired. In an embodiment according to the invention, when using two pre-catalysts, where both are activated with the same activator, useful mole percents, based upon the total moles of the pre-catalysts, are 10:90 to 0.1:99, or 25:75 to 99:1, or 50:50 to 99.5:0.5, or 50:50 to 99:1, or 75:25 to 99:1, or 90:10 to 99:1.

Monomers useful herein include substituted or unsubstituted $C_2$ to $C_{40}$ alpha olefins, or $C_2$ to $C_{20}$ alpha olefins, or $C_2$ to $C_{12}$ alpha olefins, or ethylene, propylene, butene, pentene, hexene, heptene, octene, nonene, decene, undecene, dodecene and isomers thereof. In an embodiment of the invention, the monomer comprises propylene and an optional comonomers comprising one or more ethylene or $C_4$ to $C_{40}$ olefins, or $C_4$ to $C_{20}$ olefins, or $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In an embodiment according to the invention, the monomer comprises ethylene or ethylene and a comonomer comprising one or more $C_3$ to $C_{40}$ olefins, or $C_4$ to $C_{20}$ olefins, or $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, or hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, or norbornene, norbornadiene, and dicyclopentadiene.

In an embodiment according to the invention one or more dienes are present in the polymer produced herein at up to 10 weight %, or at 0.00001 to 1.0 weight %, or 0.002 to 0.5 weight %, or 0.003 to 0.2 weight %, based upon the total weight of the composition. In an embodiment according to the invention 500 ppm or less of diene is added to the polymerization, or 400 ppm or less, or 300 ppm or less. In an embodiment according to the invention at least 50 ppm of diene is added to the polymerization, or 100 ppm or more, or 150 ppm or more.

Diolefin monomers useful in this invention include any hydrocarbon structure, or $C_4$ to $C_{30}$, having at least two unsaturated bonds, wherein at least two of the unsaturated bonds are readily incorporated into a polymer by either a stereospecific or a non-stereospecific catalyst(s). In an embodiment according to the invention, the diolefin monomers may be selected from alpha,omega-diene monomers (i.e. di-vinyl monomers). More or, the diolefin monomers are linear di-vinyl monomers, most or those containing from 4 to 30 carbon atoms. Examples of dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Cyclic dienes include cyclopentadiene, vinylnorbornene, norbornadiene, ethylidene norbornene, divinylbenzene, dicyclopentadiene or higher ring containing diolefins with or without substituents at various ring positions.

In an embodiment according to the invention, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

Polymerization processes according to the instant disclosure may be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are suitable for use herein, wherein a homogeneous polymerization process is defined to be a process where at least 90 wt % of the product is soluble in the reaction media. A bulk homogeneous process is suitable for use herein, wherein a bulk process is defined to be a process where monomer concentration in all feeds to the reactor is 70 volume % or more. In an embodiment according to the invention, no solvent or diluent is present or added in the reaction medium, (except for the small amounts used as the carrier for the catalyst system or other additives, or amounts typically found with the monomer; e.g., propane in propylene). In an embodiment according to the invention, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkyl substituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In an embodiment according to the invention, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In an embodiment according to the invention, the solvent is not aromatic, or aromatics are present in the solvent at less than 1 wt %, or less than 0.5 wt %, or less than 0.0 wt % based upon the weight of the solvents.

In an embodiment according to the invention, the feed concentration of the monomers and comonomers for the polymerization is 60 vol % solvent or less, or 40 vol % or less, or 20 vol % or less, based on the total volume of the feedstream. Or the polymerization is run in a bulk process.

Polymerizations can be run at any temperature and/or pressure suitable to obtain the desired ethylene polymers. Suitable temperatures and/or pressures include a temperature in the range of from about 0° C. to about 300° C., or about 20° C. to about 200° C., or about 35° C. to about 150° C., or from about 40° C. to about 120° C., or from about 45° C. to about 80° C.; and at a pressure in the range of from about 0.35 MPa to about 10 MPa, or from about 0.45 MPa to about 6 MPa, or from about 0.5 MPa to about 4 MPa.

In an embodiment according to the invention, the run time of the reaction is from about 0.1 minutes to about 24 hours, or up to 16 hours, or in the range of from about 5 to 250 minutes, or from about 10 to 120 minutes.

In an embodiment according to the invention, hydrogen is present in the polymerization reactor at a partial pressure of 0.001 to 50 psig (0.007 to 345 kPa), or from 0.01 to 25 psig (0.07 to 172 kPa), or 0.1 to 10 psig (0.7 to 70 kPa).

In an embodiment according to the invention, the activity of the catalyst is at least 50 g/mmol/hour, or 500 or more g/mmol/hour, or 5000 or more g/mmol/hr, or 50,000 or more g/mmol/hr. In an alternate embodiment, the conversion of olefin monomer is at least 10%, based upon polymer yield and the weight of the monomer entering the reaction zone, or 20% or more, or 30% or more, or 50% or more, or 80% or more.

In an embodiment according to the invention, the polymerization conditions include one or more of the following: 1) temperatures of 0 to 300° C. (or 25 to 150° C., or 40 to 120° C., or 45 to 80° C.); 2) a pressure of atmospheric pressure to 10 MPa (or 0.35 to 10 MPa, or from 0.45 to 6 MPa, or from 0.5 to 4 MPa); 3) the presence of an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; or where aromatics are or present in the solvent at less than 1 wt %, or less than 0.5 wt %, or at 0 wt % based upon the weight of the solvents); 4) wherein the catalyst system used in the polymerization comprises less than 0.5 mol %, or 0 mol % alumoxane, or the alumoxane is present at a molar ratio of aluminum to transition metal less than 500:1, or less than 300:1, or less than 100:1, or less than 1:1; 5) the polymerization or occurs in one reaction zone; 6) the productivity of the catalyst compound is at least 80,000 g/mmol/hr (or at least 150,000 g/mmol/hr, or at least 200,000 g/mmol/hr, or at least 250,000 g/mmol/hr, or at least 300,000 g/mmol/hr); 7) scavengers (such as trialkyl aluminum compounds) are absent (e.g., present at zero mol %) or the scavenger is present at a molar ratio of scavenger to transition metal of less than 100:1, or less than 50:1, or less than 15:1, or less than 10:1; and/or 8) optionally hydrogen is present in the polymerization reactor at a partial pressure of 0.007 to 345 kPa (0.001 to 50 psig) (or from 0.07 to 172 kPa (0.01 to 25 psig), or 0.7 to 70 kPa (0.1 to 10 psig)).

In an embodiment according to the invention, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In an embodiment according to the invention, the polymerization occurs in one reaction zone.

In an embodiment according to the invention, a process to polymerize olefins comprises contacting one or more olefins with a catalyst system according to any one or combination of embodiments disclosed herein at polymerization conditions to produce a polyolefin.

In a particular embodiment according to the invention, the polymerization conditions comprise a temperature of from about 0° C. to about 300° C., a pressure from about 0.35 MPa to about 10 MPa, and a time from about 0.1 minutes to about 24 hours. In an embodiment according to the invention, the one or more olefins comprise propylene. In an embodiment according to the invention, the polyolefin comprises at least 50 mole % propylene.

Polyolefin Products

The instant disclosure also relates to compositions of matter produced by the methods described herein.

In an embodiment according to the invention, the process described herein produces propylene homopolymers or propylene copolymers, such as propylene-ethylene and/or propylene-α-olefin (or $C_3$ to $C_{20}$) copolymers (such as propylene-hexene copolymers or propylene-octene copolymers) having a Mw/Mn of greater than 1 to 4 (or greater than 1 to 3).

Likewise, the process of this invention produces olefin polymers, or polyethylene and polypropylene homopolymers and copolymers. In an embodiment according to the invention, the polymers produced herein are homopolymers of ethylene or propylene, are copolymers of ethylene or having from 0 to 25 mole % (or from 0.5 to 20 mole %, or from 1 to 15 mole %, or from 3 to 10 mole %) of one or more $C_3$ to $C_{20}$ olefin comonomer (or $C_3$ to $C_{12}$ alpha-olefin, or propylene, butene, hexene, octene, decene, dodecene, or propylene, butene, hexene, octene), or are copolymers of propylene or having from 0 to 25 mole % (or from 0.5 to 20 mole %, or from 1 to 15 mole %, or from 3 to 10 mole %) of one or more of $C_2$ or $C_4$ to $C_{20}$ olefin comonomer (or ethylene or $C_4$ to $C_{12}$ alpha-olefin, or ethylene, butene, hexene, octene, decene, dodecene, or ethylene, butene, hexene, octene).

In an embodiment according to the invention, the polymers produced herein have an Mw of 5,000 to 1,000,000 g/mol (e.g., 25,000 to 750,000 g/mol, or 50,000 to 500,000 g/mol), and/or an Mw/Mn of greater than 1 to 40, or 1.2 to 20, or 1.3 to 10, or 1.4 to 5, or 1.5 to 4, or 1.5 to 3.

In an embodiment according to the invention, the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versa).

Unless otherwise indicated Mw, Mn, MWD are determined by GPC as described in US 2006/0173123 page 24-25, paragraphs [0334] to [0341].

In an embodiment according to the invention, the polyolefin has a concentration of meso isotactic pentads [mmmm] of greater than or equal to about 50 wt %, or 60 wt %, or 70 wt %, or 80 wt %, or 90 wt %, or greater than or equal to about 99 wt %, based on the total weight of the polymer as determined by $^{13}C$ NMR.

The polypropylene polymer preferably has some level of isotacticity and is preferably isotactic polypropylene or highly isotactic polypropylene. As used herein, "isotactic" is defined as having at least 10% isotactic pentads according to analysis by $^{13}C$ NMR. As used herein, "highly isotactic" is defined as having at least 60% isotactic pentads according to analysis by $^{13}C$ NMR.

The polypropylene polymer can have a propylene meso dyads content of 90% or more, 92% or more, 94% or more, 95% or more, 96% or more, 97% or more, or 98% or more. The isotacticity of the polypropylene polymer can be measured by $^{13}C$ NMR. For example, suitable techniques for measuring the isotacticity of the polypropylene polymer can be as discussed and described in U.S. Pat. No. 4,950,720. Expressed another way, the isotacticity of the polypropylene polymer, as measured by $^{13}C$ NMR, and expressed as pentad content, is greater than 93% or 95%, or 97% in certain embodiments.

In a particular embodiment according to the invention, the polyolefin comprises at least 50 mole % propylene, preferably at least 75 mol % propylene, preferably at least 85 mol % propylene.

In a particular embodiment according to the invention, the polyolefin comprises greater than 95 wt % isotactic polypropylene and has a melting point greater than or equal to about 158° C.

The polymer produced herein can have a heat of fusion ($H_f$, DSC second heat) from a high of 50 J/g or more, preferably 60 J/g or more, preferably 70 J/g or more, preferably 80 J/g or more, preferably 90 J/g or more, preferably about 95 J/g or more, or preferably about 100 J/g or more.

In an embodiment according to the invention, the, the polyolefin comprises at least 50 mole % propylene, e.g., isotactic polypropylene, and has a melting point $T_{melt}$ determined using differential scanning calorimetry, greater than about 145° C., e.g., from about 145° C. to about 170° C. Within this range, in an embodiment according to the invention, the polyolefin has a melting point $T_{melt}$ the of greater than or equal to about 148° C., or greater than or equal to about 150° C., or greater than or equal to about 152° C., or greater than or equal to about 154° C., or greater than or equal to about 155° C., or greater than or equal to about 156° C., or greater than or equal to about 157° C., or greater than or equal to about 158° C. In embodiments of the invention, the polyolefin has a melting point $T_{melt}$ of less than or equal to about 175° C., or less than or equal to about 170° C., or less than or equal to about 165° C., or less than or equal to about 160° C. In embodiments of the invention, the polyolefin comprises greater than 95 wt % isotactic polypropylene, or greater than 96 wt % isotactic polypropylene, or greater than 97 wt % isotactic polypropylene, or greater than 98 wt % isotactic polypropylene, up to 99.9 wt % isotactic polypropylene, by weight of the polyolefin. In particular embodiment according to the inventions, the polyolefin comprises greater than 95 wt % isotactic polypropylene and has a melting point greater than or equal to about 155° C., or wherein the polyolefin comprises greater than 98 wt % isotactic polypropylene and has a melting point greater than or equal to about 158° C.

In an embodiment according to the invention, isotactic polypropylene may be obtained by any embodiment of a process according to the instant disclosure, and may have a melting point greater than 158° C., e.g., from about 158° C. to about 165° C.

Blends

In an embodiment according to the invention, the polymer (or the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In an embodiment according to the invention, the polymer (or the polyethylene or polypropylene) is present in the above blends, at from 10 to 99 wt %, based upon the weight of the polymers in the blend, or 20 to 95 wt %, or at least 30 to 90 wt %, or at least 40 to 90 wt %, or at least 50 to 90 wt %, or at least 60 to 90 wt %, or at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX 1010 or IRGANOX 1076 available from Ciba-Geigy); phosphites (e.g., IRGAFOS 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

In an embodiment according to the invention, any of the foregoing polymers, such as the foregoing polypropylenes or blends thereof, may be used in a variety of end-use applications. Applications include, for example, mono- or multi-layer blown, extruded, and/or shrink films. These films may be formed by any number of well-known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxial orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the machine direction (MD) at a ratio of up to 15, or between 5 and 7, and in the transverse direction (TD) at a ratio of up to 15, or 7 to 9. However, In an embodiment according to the invention the film is oriented to the same extent in both the MD and TD directions.

The films may vary in thickness depending on the intended application; however, films of a thickness from 1 to 50 µm are usually suitable. Films intended for packaging are usually from 10 to 50 µm thick. The thickness of the sealing layer is typically 0.2 to 50 µm. There may be a sealing layer on both the inner and outer surfaces of the film or the sealing layer may be present on only the inner or the outer surface.

In an embodiment according to the invention, one or more layers may be modified by corona treatment, electron beam irradiation, gamma irradiation, flame treatment, or microwave. In an embodiment according to the invention, one or both of the surface layers is modified by corona treatment.

Molded Products

The compositions described herein (particularly polypropylene compositions) may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

Further, the compositions described herein (particularly polypropylene compositions) may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. Typically, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The tool stays closed to cool the film and the tool is then opened. The shaped laminate is then removed from the tool. The thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution.

Blow molding is another suitable forming means for use with the compositions of this invention, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley & Sons 1990).

Likewise, molded articles may be fabricated by injecting molten polymer into a mold that shapes and solidifies the molten polymer into desirable geometry and thickness of molded articles. Sheets may be made either by extruding a substantially flat profile from a die, onto a chill roll, or by calendaring. Sheets are generally considered to have a thickness of from 254 µm to 2540 µm (10 mils to 100 mils), although any given sheet may be substantially thicker.

Non-Wovens and Fibers

The polyolefin compositions described above may also be used to prepare nonwoven fabrics and fibers of this invention in any nonwoven fabric and fiber making process, including but not limited to, melt blowing, spunbonding, film aperturing, and staple fiber carding. A continuous filament process may also be used. Or a spunbonding process is used. The spunbonding process is well known in the art. Generally it involves the extrusion of fibers through a spinneret. These fibers are then drawn using high velocity air and laid on an endless belt. A calender roll is generally then used to heat the web and bond the fibers to one another although other techniques may be used such as sonic bonding and adhesive bonding.

EMBODIMENTS

Accordingly, the instant disclosure relates to the following embodiments:

E1. A catalyst compound represented by the formula:

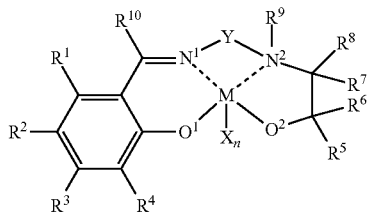

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

E2. The catalyst compound according to Embodiment E1, comprising $[O^1,N^1,N^2]$-$[N^1,N^2,O^2]$ in a fac-mer arrangement.

E3. The catalyst compound according to Embodiment E1, wherein $[O^1,N^1,N^2]$—$[N^1,N^2,O^2]$ are in a mer-fac arrangement.

E4. The catalyst compound according to Embodiment E1, wherein $[O^1,N^1,N^2]$—$[N^1,N^2,O^2]$ are in a fac-fac arrangement.

E5. The catalyst compound according to any one of Embodiments E1 to E4, wherein M is Ti, Hf or Zr.

E6. The catalyst compound according to any one of Embodiments E1 to E5, wherein each X is a benzyl radical, a halogen radical, an O-i-propyl radical or an O-tert-butyl radical.

E7. The catalyst compound according to any one of Embodiments E1 to E6, wherein X is a benzyl radical.

E8. The catalyst compound according to any one of Embodiments E1 to E7, wherein each of $R^1$, $R^2$, $R^3$, $R^4$, $R^5$, $R^6$, $R^7$, $R^8$, $R^9$ and $R^{10}$ is, independently, hydrogen, a halogen, or a $C_1$ to $C_{30}$ hydrocarbyl radical.

E9. The catalyst compound according to any one of Embodiments E1 to E8, wherein each of $R^1$, $R^2$, $R^3$, $R^4$, $R^5$, $R^6$, $R^7$, $R^8$, $R^9$ and $R^{10}$ is, independently, hydrogen, a halogen, or a $C_1$ to $C_{10}$ hydrocarbyl radical.

E10. The catalyst compound according to any one of Embodiments E1 to E9, wherein Y comprises a phenylene divalent radical.

E11. The catalyst compound according to any one of Embodiments E1 to E10, wherein Y and $R^9$ join together to form a $C_4$ to $C_{62}$ cyclic or polycyclic ring structure, wherein the catalyst compound is represented by the formula:

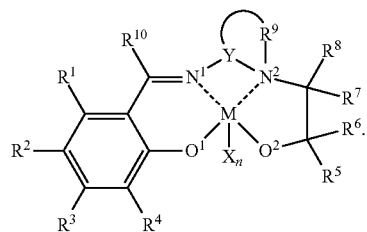

E12. The catalyst compound according to any one of Embodiments E1 to E11, wherein: each X is a benzyl radical;
at least one of $R^2$, $R^4$, $R^5$, $R^6$ and $R^9$ is independently selected from the group consisting of: $C_1$-$C_{10}$ alkyl, $C_1$-$C_{10}$ cycloalkyl, $C_1$-$C_{10}$ alkenyl, $C_1$-$C_{10}$ alkoxy, aryl substituted $C_1$-$C_{10}$ alkyl, $C_1$-$C_{10}$ aryl, halo and combinations thereof; and
$R^1$, $R^3$, $R^7$, $R^8$ and $R^{10}$ are hydrogen.

E13. The catalyst compound according to any one of Embodiments E1 to E12, wherein at least one of $R^2$, $R^4$, $R^5$, $R^6$ and $R^9$ is independently selected from the group consisting of: methyl, ethyl, isopropyl, isobutyl, tertiary-butyl, isopentyl, 2-methyl-2-phenylethyl; methoxy, benzyl, phenyl, adamantyl, chloro, bromo, iodo, perfluoro $C_1$ to $C_{10}$ alkyl, and combinations thereof.

E14. The catalyst compound according to any one of Embodiments E1 to E13, wherein:
$R^2$, $R^4$, $R^5$, $R^6$, $R^9$ or a combination thereof is chloro, bromo, iodo, a bulky ligand substitution or a combination thereof,
the bulky ligand substitution, if present, comprises a molecular volume greater than or equal to the molecular volume of a tertiary-butyl substitution; and
the bulky ligand substitution, if present, comprises a $C_4$ to $C_{20}$ hydrocarbyl radical, —$SR^1$, —$NR^2_2$, —$PR^3_2$, or a combination thereof, where each $R^1$, $R^2$ and $R^3$ is independently a $C_1$ to $C_{30}$ hydrocarbyl.

E15. The catalyst compound according to any one of Embodiments E1 to E14, represented by the formula:

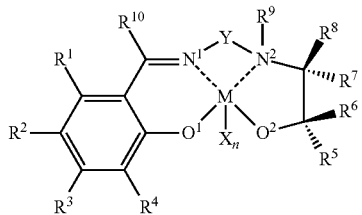

wherein $R^5$ is different than $R^6$; $R^7$ is different than $R^8$, or a combination thereof.

E16. A catalyst system comprising an activator and a catalyst compound according to any one of Embodiments E1 to E15.

E17. A catalyst system comprising an activator and a catalyst compound represented by the formula:

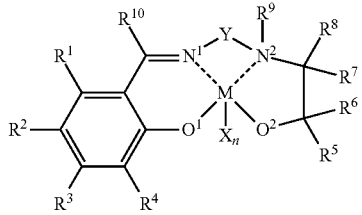

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

E18. The catalyst system according to Embodiment E16 or Embodiment E17, comprising $[O^1,N^1,N^2]$—$[N^1,N^2,O^2]$ in a fac-mer arrangement.

E19. The catalyst system according to Embodiment E16 or Embodiment E17, comprising $[O^1,N^1,N^2]$—$[N^1,N^2,O^2]$ are in a mer-fac arrangement.

E20. The catalyst system according to Embodiment E16 or Embodiment E17, comprising $[O^1,N^1,N^2]$—$[N^1,N^2,O^2]$ are in a fac-fac arrangement.

E21. The catalyst system according to any one of Embodiments E16 to E20, comprising activation rearranges $[O^1,N^1,N^2]$—$[N^1,N^2,O^2]$ into a fac-mer arrangement.

E22. The catalyst system according to any one of Embodiments E16 to E20, comprising activation rearranges $[O^1,N^1,N^2]$—$[N^1,N^2,O^2]$ into a mer-fac arrangement.

E23. The catalyst system according to any one of Embodiments E16 to E20, comprising activation rearranges $[O^1,N^1,N^2]$—$[N^1,N^2,O^2]$ into a fac-fac arrangement.

E24. The catalyst system according to any one of Embodiments E16 to E23, wherein the activator comprises alumoxane, a non-coordinating anion activator, or a combination thereof.

E25. The catalyst system according to any one of Embodiments E16 to E24, wherein the activator comprises alumoxane and the alumoxane is present at a ratio of 1 mole aluminum or more per mole of catalyst compound.

E26. The catalyst system according to any one of Embodiments E16 to E25, wherein the activator is represented by the formula: $(Z)_d^+(A^{d-})$
wherein Z is (L-H), or a reducible Lewis Acid, wherein L is a neutral Lewis base, H is hydrogen and (L-H)$^+$ is a Bronsted acid;
$A^{d-}$ is a non-coordinating anion having the charge d$^-$; and
d is an integer from 1 to 3.

E27. The catalyst system according to any one of Embodiments E16 to E26, wherein the activator is represented by the formula: $(Z)_d^+(A^{d-})$
wherein $A^{d-}$ is a non-coordinating anion having the charge d$^-$;
d is an integer from 1 to 3, and
Z is a reducible Lewis acid represented by the formula: (Ar$_3$C+), where Ar is aryl radical, an aryl radical substituted with a heteroatom, an aryl radical substituted with one or more $C_1$ to $C_{40}$ hydrocarbyl radicals, an aryl radical substituted with one or more functional groups comprising elements from Groups 13-17 of the periodic table of the elements or a combination thereof.

E28. A process to activate a catalyst system, comprising combining an activator with a catalyst compound according to any one of Embodiments E1 to E15.

E29. A process to activate a catalyst system comprising combining an activator with a catalyst compound represented by the formula:

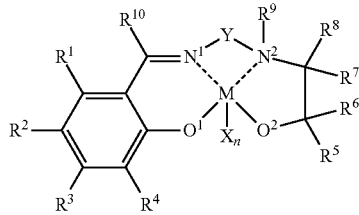

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

E30. The process according to Embodiment E28 or Embodiment E29, wherein the catalyst compound comprises [$O^1$, $N^1,N^2$]—[$N^1,N^2,O^2$] in a fac-mer arrangement.

E31. The process according to Embodiment E28 or Embodiment E29, wherein the catalyst compound comprises [$O^1$, $N^1,N^2$]—[$N^1,N^2,O^2$] are in a mer-fac arrangement.

E32. The process according to Embodiment E28 or Embodiment E29, wherein the catalyst compound comprises [$O^1$, $N^1,N^2$]—[$N^1,N^2,O^2$] are in a fac-fac arrangement.

E33. The process according to any one of Embodiments E28 to E32 wherein activation rearranges [$O^1,N^1,N^2$]—[$N^1,N^2,O^2$] into a fac-mer arrangement.

E34. The process according to any one of Embodiments E28 to E32 wherein activation rearranges [$O^1,N^1,N^2$]—[$N^1,N^2,O^2$] into a mer-fac arrangement.

E35. The process according to any one of Embodiments E28 to E32 wherein activation rearranges [$O^1,N^1,N^2$]—[$N^1,N^2,O^2$] into a fac-fac arrangement.

E36. A process to polymerize olefins comprising contacting one or more olefins with a catalyst system according to any one of Embodiments E28 to E35 at polymerization conditions to produce a polyolefin, E37. A process to polymerize olefins comprising:
contacting one or more olefins with a catalyst system at polymerization conditions to produce a polyolefin, the catalyst system comprising an activator and a catalyst compound represented by the formula:

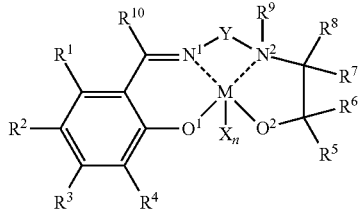

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

E38. A process to polymerize olefins comprising:
contacting a salenol ligand with a metalation reagent to produce a catalyst precursor; and
contacting the catalyst precursor with an activator and one or more olefins at polymerization conditions to produce a polyolefin;
wherein the salenol ligand is represented by the formula:

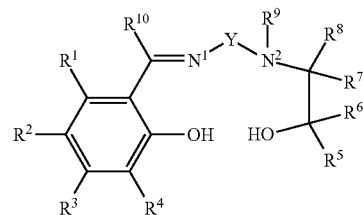

wherein the metalation reagent is represented by the formula:

$$MX^1X^2X^3X^4$$

wherein the catalyst precursor is represented by the formula:

(II)

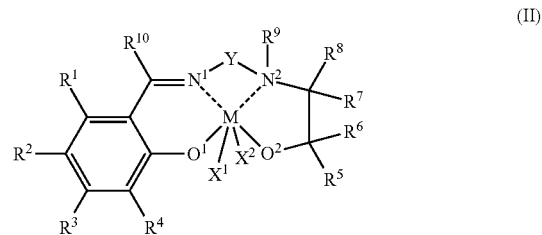

wherein each solid line represents a covalent bond and each dashed line represents a bond having varying degrees of covalency and a varying degree of coordination;
wherein M is a Group 3, 4, 5 or 6 transition metal, provided however where M is trivalent then $X^2$ is not present;
wherein $N^1$ and $N^2$ are nitrogen and $O^1$ and $O^2$ are oxygen;
wherein each of $X^1$, $X^2$, $X^3$ and $X^4$ is, independently, a univalent $C_1$ to $C_{20}$ hydrocarbyl radical, a functional group comprising elements from Groups 13-17 of the periodic table of the elements, or $X^1$ and $X^2$ (if present) may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

E39. The process according to any one of Embodiments E36 to E38, wherein the polymerization conditions comprise a temperature of from about 0° C. to about 300° C., a pressure from about 0.35 MPa to about 10 MPa, and a time from about 0.1 minutes to about 24 hours.

E40. The process according to any one of Embodiments E36 to E39, wherein the catalyst compound comprises [O¹,N¹,N²]—[N¹,N²,O²] in a fac-mer arrangement.

E41. The process according to any one of Embodiments E36 to E39, wherein the catalyst compound comprises [O¹,N¹,N²]—[N¹,N²,O²] are in a mer-fac arrangement.

E42. The process according to any one of Embodiments E36 to E39, wherein the catalyst compound comprises [O¹,N¹,N²]—[N¹,N²,O²] are in a fac-fac arrangement.

E43. The process according to any one of Embodiments E36 to E42 wherein activation rearranges [O¹,N¹,N²]—[N¹,N²,O²] into a fac-mer arrangement.

E44. The process according to any one of Embodiments E36 to E42 wherein activation rearranges [O¹,N¹,N²]—[N¹,N²,O²] into a mer-fac arrangement.

E45. The process according to any one of Embodiments E36 to E42 wherein activation rearranges [O¹,N¹,N²]—[N¹,N²,O²] into a fac-fac arrangement.

E46. The process according to any one of Embodiments E36 to E45, wherein the salenol ligand and the metalation reagent are contacted prior to combination with the activator and subsequently with the activator without isolation of the catalyst compound.

E47 The process according to any one of Embodiments E36 to E46, wherein the salenol ligand and the metalation reagent are contacted in the presence of the activator, in the presence of one or more olefins, or a combination thereof.

E48. The process according to any one of Embodiments E36 to E47, wherein the one or more olefins comprise propylene.

E49. The process according to any one of Embodiments E36 to E48, wherein the polyolefin comprises at least 50 mole % propylene.

E50. The process according to any one of Embodiments E36 to E49, wherein the polyolefin comprises greater than 95 wt % isotactic polypropylene and has a melting point greater than or equal to about 158° C.

E51. A polyolefin comprising isotactic polypropylene obtained by the process according to any one of Embodiments E36 to E50, and having a melting point greater than 158° C.

E52. A process to prepare a catalyst compound, comprising reacting a tetra-substituted metalating agent $MX_{(n+2)}$ with a salenol ligand represented by the formula:

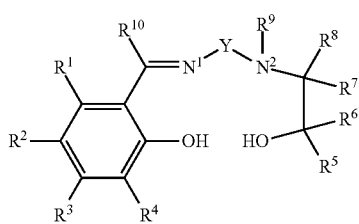

to obtain a catalyst compound represented by the formula:

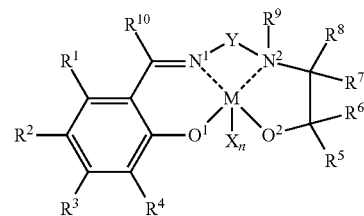

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2 depending on the valency of M;
wherein each X is, independently, a univalent $C_1$ to $C_{20}$ hydrocarbyl radical, a functional group comprising elements from Groups 13-17 of the periodic table of the elements, or where n is 2 then two of X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

E53. The process according to Embodiment E52, further comprising wrapping [O¹,N¹,N²]—[N¹,N²,O²] of the salenol ligand around the metal center M in a in a fac-mer arrangement.

E54. The process according to Embodiment E52, further comprising wrapping [O¹,N¹,N²]—[N¹,N²,O²] of the salenol ligand around the metal center M in a mer-fac arrangement.

E55. The process according to Embodiment E52, further comprising wrapping [O¹,N¹,N²]—[N¹,N²,O²] of the salenol ligand around the metal center M in a fac-fac arrangement.

E56. The process of any one of Embodiments E52 to E55, further comprising reacting a diamine Y-bridge compound NH₂—Y—NHR' with a salicylaldehyde to form an imine-Y-bridged-amine, followed by reaction of the imine-Y-bridged-amine with an epoxide to form the salenol ligand.

E57. The polyolefin obtained by the process according to any one of Embodiments E36 to E0.

E58. The polyolefin according to Embodiment E51 or Embodiment E57 comprising propylene homopolymer.

E59. The polyolefin according to Embodiment E51 or Embodiment E57 comprising propylene-ethylene and/or propylene-α-olefin ($C_4$ to $C_{20}$) copolymer.

E60. The polyolefin according to any one of Embodiments E51 and E57 to E59 comprising Mw/Mn of greater than 1 to 4.

E61. The polyolefin according to Embodiment E60 comprising Mw/Mn of greater than 1 to 3.

E62. The polyolefin according to any one of Embodiments E51 and E57 to E61 comprising a concentration of meso isotactic pentads [mmmm] of greater than or equal to about 50 wt %, based on the total weight of the polymer as determined by ¹³C NMR.

E63. The polyolefin according to Embodiment E62 wherein the concentration of meso isotactic pentads [mmmm] is greater than or equal to about 60 wt %.

E64. The polyolefin according to Embodiment E62 wherein the concentration of meso isotactic pentads [mmmm] is greater than or equal to about 70 wt %.

E65. The polyolefin according to Embodiment E62 wherein the concentration of meso isotactic pentads [mmmm] is greater than or equal to about 80 wt %.

E66. The polyolefin according to Embodiment E62 wherein the concentration of meso isotactic pentads [mmmm] is greater than or equal to about 90 wt %.

E67. The polyolefin according to Embodiment E62 wherein the concentration of meso isotactic pentads [mmmm] is greater than or equal to about 99 wt %.

E68. The polyolefin according to any one of Embodiments E51 and E57 to E67 comprising an Mw of 5,000 to 1,000,000 g/mol.

E69. The polyolefin according to Embodiment E68 comprising an Mw of 25,000 to 750,000 g/mol.

E70. The polyolefin according to Embodiment E68 comprising an Mw of 50,000 to 500,000 g/mol.

E71. The polyolefin according to any one of Embodiments E51 and E57 to E70 comprising an Mw/Mn of greater than 1 to 40.

E72. The polyolefin according to Embodiment E71 comprising an Mw/Mn of 1.2 to 20.

E73. The polyolefin according to Embodiment E71 comprising an Mw/Mn of 1.3 to 10.

E74. The polyolefin according to Embodiment E71 comprising an Mw/Mn of 1.4 to 5.

E75. The polyolefin according to Embodiment E71 comprising an Mw/Mn of 1.5 to 4.

E76. The polyolefin according to Embodiment E71 comprising an Mw/Mn of 1.5 to 3.

E77. The polyolefin according to any one of Embodiments E51 and E57 to E76 comprising a unimodal molecular weight distribution as determined by Gel Permeation Chromatography (GPC).

E78. The polyolefin according to any one of Embodiments E51 and E57 to E76 comprising a multimodal molecular weight distribution as determined by Gel Permeation Chromatography (GPC).

E79. The polyolefin according to any one of Embodiments E51 and E57 to E78 comprising a heat of fusion (DSC second heat) of 50 J/g or more.

E80. The polyolefin according to any one of Embodiments E51 and E57 to E78 comprising a heat of fusion (DSC second heat) of 60 J/g or more.

E81. The polyolefin according to any one of Embodiments E51 and E57 to E78 comprising a heat of fusion (DSC second heat) of 70 J/g or more.

E82. The polyolefin according to any one of Embodiments E51 and E57 to E78 comprising a heat of fusion (DSC second heat) of 80 J/g or more.

E83. The polyolefin according to any one of Embodiments E51 and E57 to E78 comprising a heat of fusion (DSC second heat) of 90 J/g or more.

E84. The polyolefin according to any one of Embodiments E51 and E57 to E78 comprising a heat of fusion (DSC second heat) of 100 J/g or more.

E85. The polyolefin according to any one of Embodiments E51 and E57 to E78 comprising a heat of fusion (DSC second heat) of 95 J/g or more.

E86. The polyolefin according to any one of Embodiments E51 and E57 to E85 comprising a melting point $T_{melt}$ determined using differential scanning calorimetry from about 145° C. to about 170° C.

E87. The polyolefin according to Embodiment E86 wherein the $T_{melt}$ is greater than or equal to about 148° C.

E88. The polyolefin according to Embodiment E86 wherein the $T_{melt}$ is greater than or equal to about 150° C.

E89. The polyolefin according to Embodiment E86 wherein the $T_{melt}$ is greater than or equal to about 152° C.

E90. The polyolefin according to Embodiment E86 wherein the $T_{melt}$ is greater than or equal to about 154° C.

E91. The polyolefin according to Embodiment E86 wherein the $T_{melt}$ is greater than or equal to about 155° C.

E92. The polyolefin according to Embodiment E86 wherein the $T_{melt}$ is greater than or equal to about 156° C.

E93. The polyolefin according to Embodiment E86 wherein the $T_{melt}$ is greater than or equal to about 157° C.

E94. The polyolefin according to Embodiment E86 wherein the $T_{melt}$ is greater than or equal to about 158° C.

E95. The polyolefin according to any one of Embodiments E86 to E94 wherein the $T_{melt}$ is less than or equal to about 165° C.

E96. The polyolefin according to any one of Embodiments E86 to E94 wherein the $T_{melt}$ is less than or equal to about 160° C.

EXAMPLES

The foregoing discussion can be further described with reference to the following non-limiting examples.

Eleven illustrative catalyst compounds (A through K) of the invention, each according to one or more embodiments described, were synthesized consistent with the procedure described below. Four of the exemplary catalysts were used to polymerize olefins as described below. All reactions were carried out at room temperature (25° C.) under a purified nitrogen atmosphere using standard glovebox, high vacuum or Schlenk techniques, unless otherwise noted. All solvents used were anhydrous, de-oxygenated and purified according to known procedures. All starting materials were either purchased from Aldrich and purified prior to use or prepared according to procedures known to those skilled in the art.

Synthesis of the Salenol Ligand According to Example C—$H_2$:

A solution of 2,2-diphenyl oxirane (0.14 gram, 0.68 mmol) in methanol (20 mL) was added to a solution of 2-((methylamino)ethylimino)methyl)-4-methyl-6-adamantylphenol (0.22 gram, 0.68 mmol) in methanol (20 mL) and the reaction mixture was stirred for 12 hours at 90° C. in closed high pressure vessel. Then the solvent was removed under vacuum. The crude product was re-crystallized from cold methanol yielding the ligand precursor C—$H_2$ as a yellow solid quantitatively.

$^1$H NMR (CDCl$_3$, 400 MHz): δ=8.16 (s, 1H, NCH), 7.49 (d, 1H, J=1.8 Hz, ArH), 7.43-7.34 (m, 3H, ArH), 7.30 (d, 1H, J=1.8 Hz, ArH), 7.26-7.20 (m, 3H, ArH), 7.17-7.15 (m, 2H, ArH), 7.06-7.04 (m, 2H, ArH), 3.55 (t, 2H, J=6.2 Hz, NCH$_2$), 3.34 (s, 2H, NCH$_2$), 2.67 (t, 2H, J=6.2 Hz, NCH$_2$), 2.34 (s, 3H, NCH$_3$), 2.18 (bs, 6H, Adamantyl), 2.14 (s, 3H, ArCH$_3$), 2.07 (bs, 3H, Adamantyl), 1.78 (m, 6H, Adamantyl).

$^{13}$C NMR (CDCl$_3$, 100.67 MHz): δ=167.4 (CN), 159.7 (CO), 147.7 (C), 138.1 (C), 130.9 (CH), 129.6 (CH), 129.3 (CH), 128.8 (4CH), 128.2 (2C), 127.3 (2CH), 126.4 (4CH), 119.0 (C), 75.2 (C—OH), 68.6 (NCH$_2$), 60.2 (CH$_2$), 57.9 (CH$_2$), 44.7 (NCH$_3$), 41.0 (CH$_2$, Ad), 37.9 (CH$_2$, Ad), 37.6 (CH, Ad), 29.8 (CH, Ad), 21.5 (CH$_3$).

Synthesis of the Salenol Ligand According to Example F—H$_2$:

A solution of 2,2-diphenyl oxirane (0.37 gram, 1.76 mmol) in methanol (20 mL) was added to a solution of 2-((S)-(aminomethyl)pyrrolidine)-4-methyl-6-adamantylphenol (0.62 gram, 1.76 mmol) in methanol (20 mL) and the reaction mixture was stirred for 12 hours at 90° C. in closed high pressure vessel. Then the solvent was removed under vacuum. The crude product was re-crystallized from cold methanol yielding the ligand precursor F—H$_2$ as a yellow solid quantitatively.

$^1$H NMR (CDCl$_3$, 400 MHz): δ=8.20 (s, 1H, NCH), 7.55 (d, 1H, J=1.3 Hz, ArH), 7.32 (d, 1H, J=1.3 Hz, ArH), 7.16-7.02 (m, 10H, ArH), 3.71 (d, 1H, J=10.2 Hz, CH), 3.68 (m, 1H, CH), 3.53 (m, 1H, CH), 3.49 (d, 1H, J=10.2 Hz, CH), 3.38 (m, 1H, CH), 2.53 (m, H, CH), 2.45 (m, H, CH), 2.24 (s, 3H, CH$_3$), 2.18 (bs, 6H, Adamantyl), 2.03 (bs, 3H, Adamantyl), 1.78 (m, 6H, Adamantyl), 1.55 (m, 2H, CH).

$^{13}$C NMR (CDCl$_3$, 100.67 MHz): δ=167.6 (CN), 159.3 (CO), 144.9 (C), 135.6 (C), 132.2 (CH), 130.8 (CH), 130.2 (CH), 128.7 (4CH), 127.1 (2C), 126.3 (2CH), 126.1 (4CH), 119.3 (C), 75.0 (C—OH), 66.7 (NCH$_2$), 64.9 (C), 56.7 (CH$_2$), 52.9 (CH$_2$), 40.9 (CH$_2$, Ad), 37.9 (CH$_2$, Ad), 37.6 (CH, Ad), 29.8 (CH, Ad), 25.5 (CH$_2$), 34.6 (CH$_2$), 21.4 (CH$_3$).

Synthesis of Example C—Ti—Bn$_2$:

Example C—H$_2$ (40 mg, 0.07 mmol) was dissolved in about 1 mL of toluene and added dropwise to a stirring red solution of TiBn$_4$ (32 mg, 0.07 mmol) in about 1 mL of toluene. The color of the solution changed to dark red-brown. The reaction mixture was allowed to warm to room temperature, and after 15 minutes of stirring the solvent was removed under vacuum, yielding a brown solid, which was washed with about 1 mL of pentane and dried in vacuo. The final yield was 49 mg (86%).

$^1$H NMR (C$_6$D$_6$, 400 MHz): δ=7.39 (s, 1H, NCH), 7.07 (d, 1H, J=1.6 Hz, ArH), 6.98-6.81 (m, 20H, ArH), 6.48 (d, 1H, J=1.6 Hz, ArH), 5.41 (d, J=11.8 Hz, 1H), 3.90 (d, J=13.4 Hz, 1H, CH), 3.52-3.12 (m, 4H, CH), 3.51 (d, J=12.8 Hz, 1H, CH), 3.48-2.74 (m, 9H, CH), 2.41 (m, 9H, Adamantyl), 2.19 (s, 3H, ArCH$_3$), 1.85 (m, 6H, Adamantyl).

Polymerization of Liquid Propylene:

A stainless steel reactor equipped with an inner glass sleeve and a magnetic stir-bar was charged with 10 μmol of the Example C—Ti—Bn$_2$ catalyst and 500 equiv of dried MAO and was cooled with a liquid nitrogen bath. A measured volume of propylene was condensed, the reactor was sealed, and was allowed to warm to RT. The polymerisation was pursued for 13 h. The total weight of the monomer and formed polymer were measured, and the remaining monomer was released. The polymer was treated with acidified methanol solution (5% HCl solution) and petroleum ether. The insoluble polymers were obtained by filtration and were dried in air.

$^{13}$C NMR (o-Cl-benzene-d$_4$, 125 MHz, 430K): δ=46.10 (CH$_2$), 28.44 (CH), 21.85 (CH$_3$). T$_m$ measured by DSC=163.3° C. (ΔH=79.4 J/g), [mmmm]=99%.

Solution Polymerization:

Generally, polymerization was performed using propylene of an initial pressure of 231 kPa (33.5 psig) dissolved in 70 mL of toluene as described above.

Example A

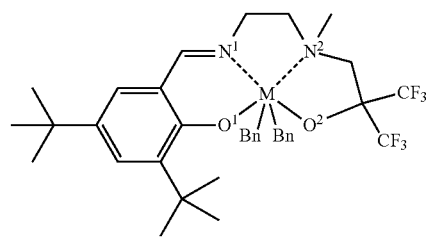

M = Hf, Zr, Ti

Example B

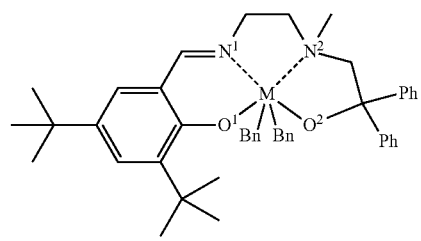

M = Hf, Zr, Ti

Example C

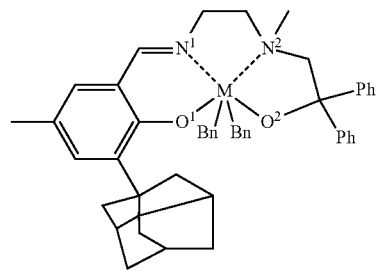

M = Hf, Zr, Ti

Example D
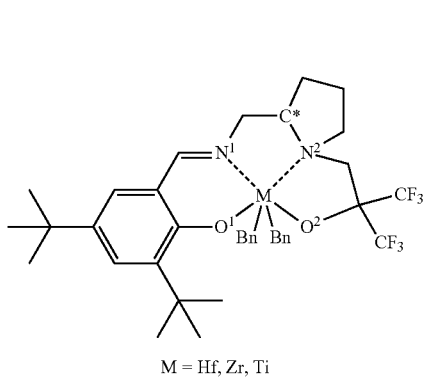
M = Hf, Zr, Ti
Example E
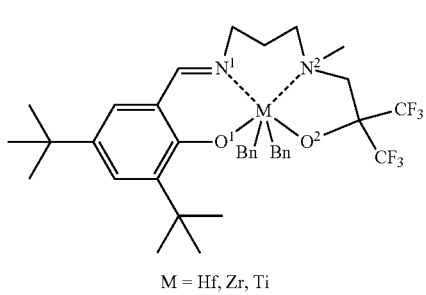
M = Hf, Zr, Ti
Example F
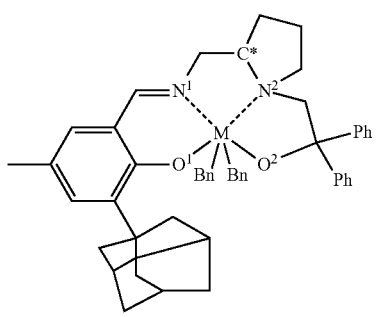
M = Hf, Zr, Ti
Example G
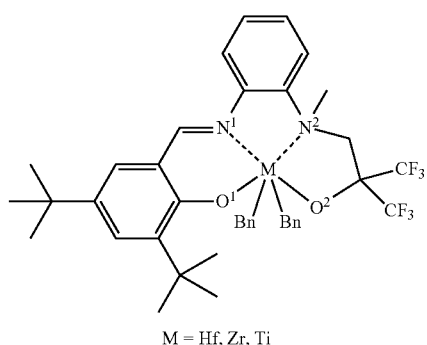
M = Hf, Zr, Ti
Example H
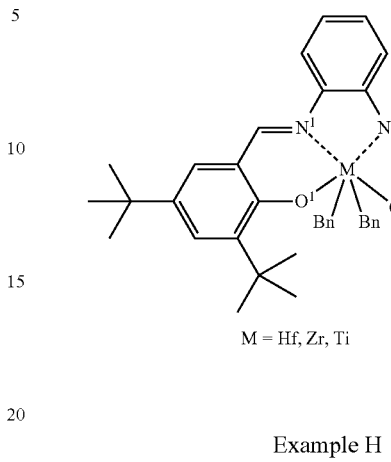
M = Hf, Zr, Ti
Example I
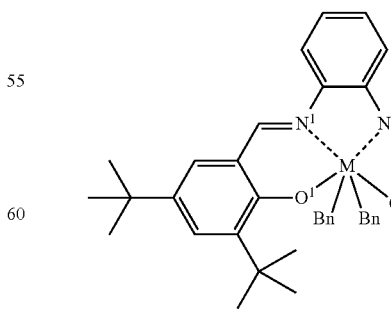
M = Hf, Zr, Ti Example J

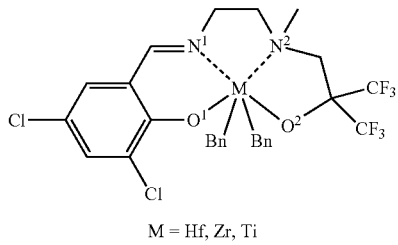

M = Hf, Zr, Ti

Example K

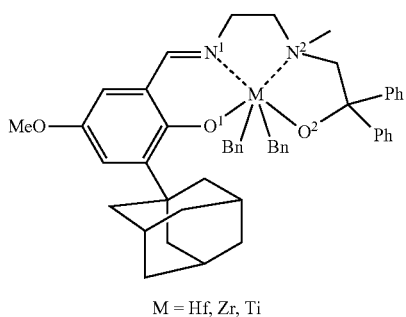

M = Hf, Zr, Ti

Molecular structure as determined by single crystal X-ray diffraction of the salenol ligands of Examples A, G, and J are shown in FIGS. 1, 2, 3, and 4, respectively.

FIG. 1 shows the X-ray crystal structure of the salenol catalyst according to Example A, where the metal is Hf and where the benzyl groups are replaced by O-t-Bu according to the following formula:

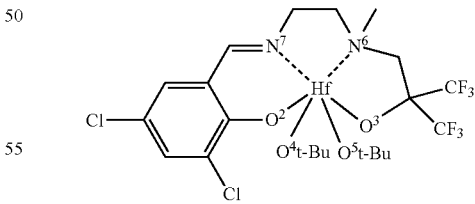

The structure in FIG. 1 is shown with the tertiary butyl group of each of the tertiary butoxy groups omitted for clarity.

Figure 2:
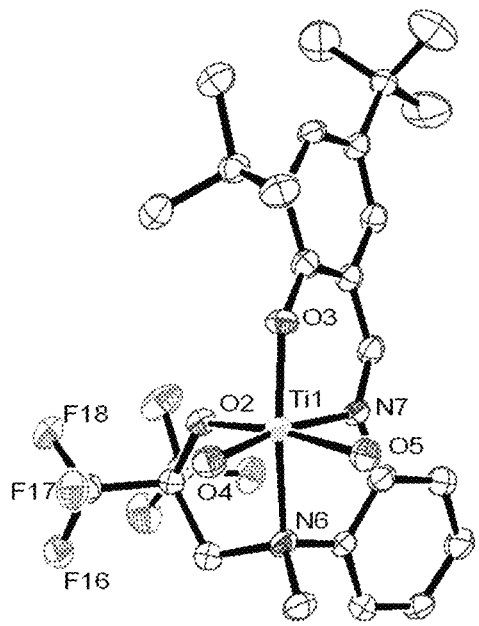
FIG. 2 is a representation of molecular structure as determined by single crystal X-ray diffraction according to the inventive embodiment of Example G-Ti(O-i-PO$_2$.

FIG. 2 shows the X-ray crystal structure of the salenol catalyst according to Example G, where the metal is Ti and where the benzyl groups are replaced by O-i-Pr according to the following formula:

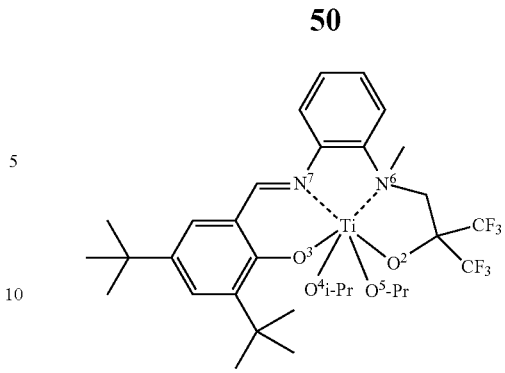

The structure in FIG. 2 is shown with the isopropyl group of each of the isopropoxy groups omitted for clarity.

Figure 3:
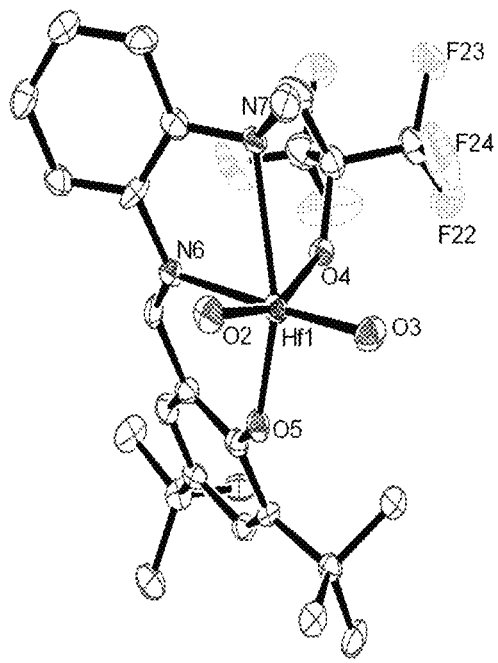
FIG. 3 is a representation of molecular structure as determined by single crystal X-ray diffraction according to the inventive embodiment of Example G-Hf(O-tert-Bu)$_2$.

FIG. 3 shows the X-ray crystal structure of the salenol catalyst according to Example G, where the metal is Hf and where the benzyl groups are replaced by O-t-Bu according to the following formula:

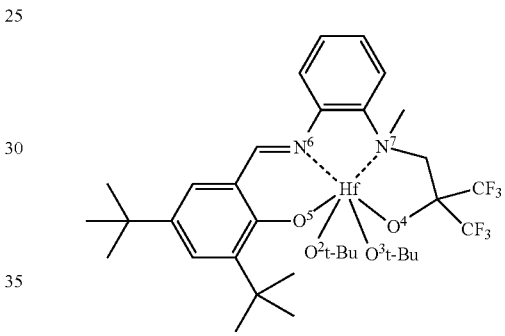

The structure in FIG. 3 is shown with the tertiary butyl group of each of the tertiary butoxy groups omitted for clarity.

Figure 4:
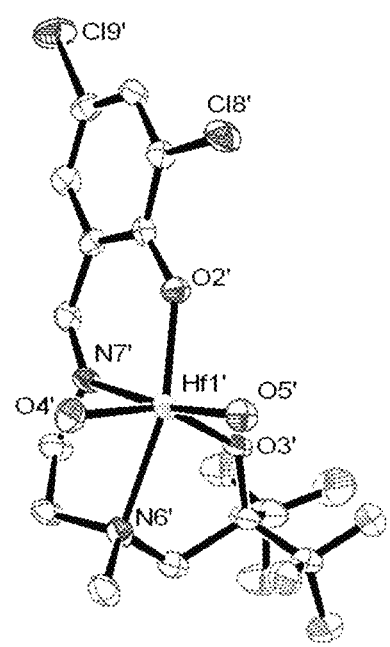
FIG. 4 is a representation of molecular structure as determined by single crystal X-ray diffraction according to the inventive embodiment of Example J-Hf(O-tert-Bu)$_2$.

FIG. 4 shows the X-ray crystal structure of the salenol catalyst according to Example J, where the metal is Hf and where the benzyl groups are replaced by O-t-Bu according to the following formula:

The structure in FIG. 4 is shown with the tertiary butyl group of each of the tertiary butoxy groups omitted for clarity.

As the figures show, the salenol ligands according to embodiments of the invention can produce catalysts having a fac-mer wrapping conformation.

A series of polymerization reactions were conducted using neat propylene and 500 eq. MAO at room temperature (25° C.) for 13 hours. The data are shown in Table 1.

TABLE 1

| Cat. Ex. | Metal | $C_3=$ used (g) | Polymer obtained (g) | $T_{melt}$ (°C.) | ΔH (J/g) | [mmmm] (wt %) |
|---|---|---|---|---|---|---|
| A | Ti | 6.94 | 1.40 | Atactic | — | Atactic |
| A | Zr | 7.27 | 2.33 | Atactic | — | Atactic |
| B | Ti | 7.02 | 0.35 insoluble 2.28 soluble | 160.6 | 22.4 | — |
| F | Ti | 7.03 | 1.35 | 158.9 | 37.0 | — |
| C | Ti | 6.84 | 0.81 | 163.3 | 79.4 | ~99 |

Neat propylene was polymerized using 10 micromoles of Example Catalyst F where M is titanium. The catalyst was activated with 500 equivalents of MAO and the polymerization was conducted at 25° C. in 70 ml toluene. The data are shown in Table 2.

TABLE 2

| Catalyst Used (mg) | Metal | Time (h) | Polymer obtained (g) | $T_{melt}$ (°C.) | Activity (g mmol$^{-1}$ h$^{-1}$) |
|---|---|---|---|---|---|
| 9 mg | Ti | 1 | 0.327 | 158.8 | 37.5 |

As the data show, the catalyst compounds, catalyst systems, and polymerization processes disclosed herein provide novel and improved catalyst and systems for the polymerization of olefins, which produce polymers having improved properties, such as high polymer melting point and highly isotactic polymers.

The catalysts in an embodiment of the invention provide improvement in catalyst activity, produce polymers with improved properties or both. In an embodiment according to the invention crystallographic techniques indicate that the appended ring system or systems are oriented fac-mer. In an embodiment according to the invention these catalysts have a structure to provide a broad corridor for the polymeryl moiety to reside and for the monomer to insert during the polymerization process. As such, catalysts according to embodiments of the instant disclosure provide for an ability to control one or more characteristics of polymerization, tacticity, comonomer insertion, and the like.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby.

What is claimed is:

1. A catalyst compound represented by the formula:

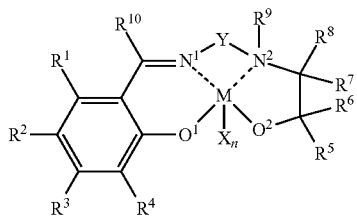

wherein each solid line represents a covalent bond and each dashed line represents a bond having varying degrees of covalency and a varying degree of coordination;

wherein M is a Group 3, 4, 5 or 6 transition metal;

wherein $N^1$ and $N^2$ are nitrogen and $O^1$ and $O^2$ are oxygen;

wherein n is 1 or 2;

wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;

wherein Y is selected from the group consisting of divalent $C_1$ to $C_{20}$ hydrocarbyl radicals, divalent functional groups comprising elements from Groups 13-17 of the periodic table of the elements, and combinations thereof; and wherein each of $R^1$, $R^2$, $R^3$, $R^4$, $R^5$, $R^6$, $R^7$, $R^8$, $R^9$ and $R^{10}$ is, independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

2. The catalyst compound of claim 1, wherein n is 2 and comprising [$O^1$,$N^1$,$N^2$]—[$N^1$,$N^2$,$O^2$] in a fac-mer, a mer-fac, or a fac-fac arrangement.

3. The catalyst compound of claim 1, wherein M is Ti, Hf or Zr.

4. The catalyst compound of claim 1, wherein X is a benzyl radical.

5. The catalyst compound of claim 1, wherein each of $R^1$, $R^2$, $R^3$, $R^4$, $R^5$, $R^6$, $R^7$, $R^8$, $R^9$ and $R^{10}$ is, independently, hydrogen, a halogen, or a $C_1$ to $C_{10}$ hydrocarbyl radical.

6. The catalyst compound of claim 1, wherein Y comprises a phenylene divalent radical.

7. The catalyst compound of claim 1, wherein Y and $R^9$ join together to form a $C_4$ to $C_{62}$ cyclic or polycyclic ring structure, represented by the formula:

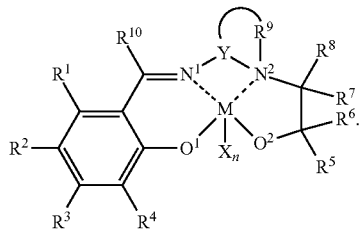

8. The catalyst compound of claim 1 wherein:

each X is a benzyl radical;

at least one of $R^2$, $R^4$, $R^5$, $R^6$ and $R^9$ is independently selected from the group consisting of: $C_1$-$C_{10}$ alkyl, $C_1$-$C_{10}$ cycloalkyl, $C_1$-$C_{10}$ alkenyl, $C_1$-$C_{10}$ alkoxy, aryl substituted $C_1$-$C_{10}$ alkyl, $C_1$-$C_{10}$ aryl, halo and combinations thereof; and $R^1$, $R^3$, $R^7$, $R^8$ and $R^{10}$ are hydrogen.

9. The catalyst compound of claim 8, wherein at least one of $R^2$, $R^4$, $R^5$, $R^6$ and $R^9$ is independently selected from the group consisting of: methyl, ethyl, isopropyl, isobutyl, tertiary-butyl, isopentyl, 2-methyl-2-phenylethyl; methoxy, benzyl, phenyl, adamantyl, chloro, bromo, iodo, perfluoro $C_1$ to $C_{10}$ alkyl, and combinations thereof.

10. The catalyst compound of claim 1, wherein:
$R^2$, $R^4$, $R^5$, $R^6$, $R^9$ or a combination thereof is chloro, bromo, iodo, a bulky ligand substitution or a combination thereof;
the bulky ligand substitution comprises a molecular volume greater than or equal to the molecular volume of a tertiary-butyl substitution; and
the bulky ligand substitution comprise a $C_4$ to $C_{20}$ hydrocarbyl radical, $-SR^{10}$, $-NR^{11}_2$, $-PR^{12}_2$, or a combination thereof, where each $R^{10}$, $R^{11}$ and $R^{12}$ is independently a $C_1$ to $C_{30}$ hydrocarbyl.

11. The catalyst compound of claim 1 represented by the formula:

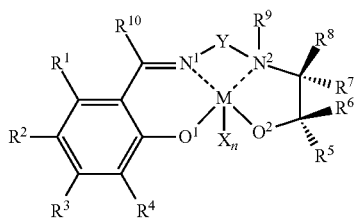

wherein $R^5$ is different than $R^6$; $R^7$ is different than $R^8$, or a combination thereof.

12. A catalyst system, comprising an activator and a catalyst compound represented by the formula:

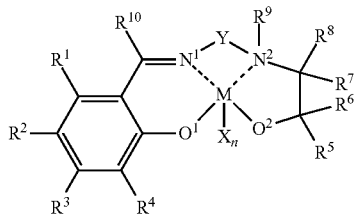

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is, independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

13. The catalyst system of claim 12, wherein n is 2 and comprising $[O^1,N^1,N^2]-[N^1,N^2,O^2]$ in a fac-mer, a mer-fac, or a fac-fac arrangement; or wherein activation rearranges $[O^1,N^1,N^2]-[N^1,N^2,O^2]$ into a fac-mer, a mer-fac, or a fac-fac arrangement.

14. The catalyst system of claim 12, wherein the activator comprises alumoxane, a non-coordinating anion activator, or a combination thereof.

15. The catalyst system of claim 12, wherein the activator comprises alumoxane and the alumoxane is present at a ratio of 1 mole aluminum or more per mole of catalyst compound.

16. The catalyst system of claim 12, wherein the activator is represented by the formula:

$$(Z)_d^+(A^{d-})$$

wherein Z is (L-H), or a reducible Lewis Acid, wherein L is a neutral Lewis base, H is hydrogen and $(L-H)^+$ is a Bronsted acid;
$A^{d-}$ is a non-coordinating anion having the charge $d^-$; and
d is an integer from 1 to 3.

17. The catalyst system of claim 12, wherein the activator is represented by the formula:

$$(Z)_d^+(A^{d-})$$

wherein $A^{d-}$ is a non-coordinating anion having the charge $d^-$;
d is an integer from 1 to 3, and
Z is a reducible Lewis acid represented by the formula: $(Ar_3C^+)$, where Ar is aryl radical, an aryl radical substituted with a heteroatom, an aryl radical substituted with one or more $C_1$ to $C_{40}$ hydrocarbyl radicals, an aryl radical substituted with one or more functional groups comprising elements from Groups 13-17 of the periodic table of the elements or a combination thereof.

18. A process to activate a catalyst system, comprising combining an activator with a catalyst compound represented by the formula:

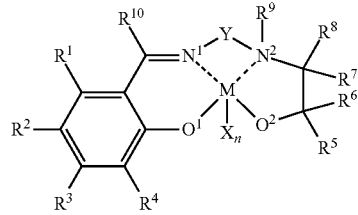

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is, independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

19. The process of claim 18, wherein n is 2 and the catalyst compound comprises [$O^1,N^1,N^2$]—[$N^1,N^2,O^2$] in a fac-mer, a mer-fac, or a fac-fac arrangement; or wherein activation rearranges [$O^1,N^1,N^2$]—[$N^1,N^2,O^2$] into a fac-mer, a mer-fac, or a fac-fac arrangement.

20. A process to polymerize olefins comprising:
contacting one or more olefins with a catalyst system at polymerization conditions to produce a polyolefin, the catalyst system comprising an activator and a catalyst compound represented by the formula:

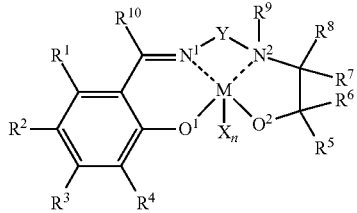

wherein each solid line represents a covalent bond and each dashed line represents a bond having varying degrees of covalency and a varying degree of coordination;
wherein M is a Group 3, 4, 5 or 6 transition metal;
wherein $N^1$ and $N^2$ are nitrogen and $O^1$ and $O^2$ are oxygen;
wherein n is 1 or 2;
wherein each X is, independently, a univalent $C_1$ to $C_{20}$ hydrocarbyl radical, a functional group comprising elements from Groups 13-17 of the periodic table of the elements, or where n is 2 each X may join together to form a $C_4$ to $C_{62}$ cyclic or polycyclic ring structure;
wherein Y is selected from the group consisting of divalent $C_1$ to $C_{20}$ hydrocarbyl radicals, divalent functional groups comprising elements from Groups 13-17 of the periodic table of the elements, and combinations thereof; and
wherein each of $R^1$, $R^2$, $R^3$, $R^4$, $R^5$, $R^6$, $R^7$, $R^8$, $R^9$ and $R^{10}$ is, independently, a hydrogen, a $C_1$-$C_{40}$ hydrocarbyl radical, a functional group comprising elements from Group 13-17 of the periodic table of the elements, or two or more of $R^1$ to $R^{10}$ and Y may independently join together to form a $C_4$ to $C_{62}$ cyclic or polycyclic ring structure.

21. The process of claim 20, wherein n is 2 and the catalyst compound comprises [$O^1,N^1,N^2$]—[$N^1,N^2,O^2$] in a fac-mer, a mer-fac, or a fac-fac arrangement; or wherein activation rearranges [$O^1,N^1,N^2$]—[$N^1,N^2,O^2$] into a fac-mer, a mer-fac, or a fac-fac arrangement.

22. The process of claim 20, wherein the polymerization conditions comprise a temperature of from about 0° C. to about 300° C., a pressure from about 0.35 MPa to about 10 MPa, and a time from about 0.1 minutes to about 24 hours.

23. The process of claim 20, wherein the one or more olefins comprise propylene.

24. The process of claim 20, wherein the polyolefin comprises at least 50 mole % propylene.

25. The process of claim 20 wherein the polyolefin comprises isotactic polypropylene having a melting point greater than 158° C.

* * * * *